(12) United States Patent
Chuang et al.

(10) Patent No.: US 10,194,108 B2
(45) Date of Patent: Jan. 29, 2019

(54) SENSOR WITH ELECTRICALLY CONTROLLABLE APERTURE FOR INSPECTION AND METROLOGY SYSTEMS

(71) Applicant: KLA-Tencor Corporation, Milpitas, CA (US)

(72) Inventors: Yung-Ho Alex Chuang, Cupertino, CA (US); John Fielden, Los Altos, CA (US); David L. Brown, Los Gatos, CA (US); Jingjing Zhang, San Jose, CA (US); Keith Lyon, Mountain View, CA (US); Mark Shi Wang, San Ramon, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/806,913

(22) Filed: Nov. 8, 2017

(65) Prior Publication Data
US 2018/0070040 A1 Mar. 8, 2018

Related U.S. Application Data

(63) Continuation of application No. 15/153,543, filed on May 12, 2016, now Pat. No. 9,860,466.
(Continued)

(51) Int. Cl.
*G01N 21/00* (2006.01)
*H04N 5/3722* (2011.01)
*G01N 21/956* (2006.01)

(52) U.S. Cl.
CPC ......... *H04N 5/3722* (2013.01); *G01N 21/956* (2013.01); *G01N 2201/12* (2013.01)

(58) Field of Classification Search
CPC .......... G01N 21/9501; G01N 21/9503; G01N 2201/12; G01N 2201/125
(Continued)

(56) References Cited

U.S. PATENT DOCUMENTS

| 3,870,917 A | 3/1975 | Cuny |
| 3,947,707 A | 3/1976 | Shannon et al. |

(Continued)

FOREIGN PATENT DOCUMENTS

| EP | 0543629 A1 | 5/1993 |
| EP | 0602983 A1 | 6/1994 |

(Continued)

OTHER PUBLICATIONS

U.S. Appl. No. 61/720,700—Certified Copy corres to PCT/EP2013/071080, pp. 1-44.
(Continued)

*Primary Examiner* — Kevin Pyo
(74) *Attorney, Agent, or Firm* — Bever, Hoffman & Harms, LLP

(57) ABSTRACT

Pixel aperture size adjustment in a linear sensor is achieved by applying more negative control voltages to central regions of the pixel's resistive control gate, and applying more positive control voltages to the gate's end portions. These control voltages cause the resistive control gate to generate an electric field that drives photoelectrons generated in a selected portion of the pixel's light sensitive region into a charge accumulation region for subsequent measurement, and drives photoelectrons generated in other portions of the pixel's light sensitive region away from the charge accumulation region for subsequent discard or simultaneous readout. A system utilizes optics to direct light received at different angles or locations from a sample into corresponding different portions of each pixel's light sensitive region.
(Continued)

Multiple aperture control electrodes are selectively actuated to collect/measure light received from either narrow or wide ranges of angles or locations, thereby enabling rapid image data adjustment.

20 Claims, 11 Drawing Sheets

Related U.S. Application Data

(60) Provisional application No. 62/172,242, filed on Jun. 8, 2015, provisional application No. 62/161,450, filed on May 14, 2015.

(58) Field of Classification Search
USPC ............... 250/221, 559.05, 559.07; 356/601
See application file for complete search history.

(56) References Cited

U.S. PATENT DOCUMENTS

| | | |
|---|---|---|
| 4,099,198 A | 7/1978 | Howorth et al. |
| 4,106,046 A | 8/1978 | Nathanson et al. |
| 4,210,922 A | 7/1980 | Shannon |
| 4,275,326 A | 6/1981 | Houtkamp |
| 4,280,141 A | 7/1981 | McCann et al. |
| 4,348,690 A | 9/1982 | Jastrzebski et al. |
| 4,382,267 A | 5/1983 | Angle |
| 4,467,189 A | 8/1984 | Tsuchiya |
| 4,555,731 A | 11/1985 | Zinchuk |
| 4,580,155 A | 4/1986 | Tsoi et al. |
| 4,644,221 A | 2/1987 | Gutierrez et al. |
| 4,760,031 A | 7/1988 | Janesick |
| 4,853,595 A | 8/1989 | Alfano et al. |
| 4,999,014 A | 3/1991 | Gold et al. |
| 5,054,683 A | 10/1991 | Haisma et al. |
| 5,120,949 A | 6/1992 | Tomasetti |
| 5,144,630 A | 9/1992 | Lin |
| 5,181,080 A | 1/1993 | Fanton et al. |
| 5,227,313 A | 7/1993 | Gluck et al. |
| 5,315,126 A | 5/1994 | Field |
| 5,376,810 A | 12/1994 | Hoenk et al. |
| 5,428,392 A | 6/1995 | Castro et al. |
| 5,440,648 A | 8/1995 | Roberts et al. |
| 5,483,378 A | 1/1996 | Rahn |
| 5,563,702 A | 10/1996 | Emery et al. |
| 5,608,526 A | 3/1997 | Piwonka-Corle et al. |
| 5,684,583 A | 11/1997 | Abe et al. |
| 5,717,518 A | 2/1998 | Shafer et al. |
| 5,719,069 A | 2/1998 | Sparks |
| 5,731,584 A | 3/1998 | Beyne et al. |
| 5,742,626 A | 4/1998 | Mead et al. |
| 5,760,809 A | 6/1998 | Malhotra et al. |
| 5,760,899 A | 6/1998 | Eismann |
| 5,812,190 A | 9/1998 | Audier et al. |
| 5,852,322 A | 12/1998 | Speckbacher |
| 5,877,859 A | 3/1999 | Aspnes et al. |
| 5,940,685 A | 8/1999 | Loomis et al. |
| 5,965,910 A | 10/1999 | Wood |
| 5,999,310 A | 12/1999 | Shafer et al. |
| 6,013,399 A | 1/2000 | Nguyen |
| 6,030,852 A | 2/2000 | Sano et al. |
| 6,064,759 A | 5/2000 | Buckley et al. |
| 6,162,707 A | 12/2000 | Dinh et al. |
| 6,201,601 B1 | 3/2001 | Vaez-Iravani et al. |
| 6,271,916 B1 | 8/2001 | Marxer et al. |
| 6,278,119 B1 | 8/2001 | Nikzad et al. |
| 6,285,018 B1 | 9/2001 | Aebi et al. |
| 6,297,879 B1 | 10/2001 | Yang et al. |
| 6,297,880 B1 | 10/2001 | Rosencwaig et al. |
| 6,307,586 B1 | 10/2001 | Costello |
| 6,346,700 B1 | 2/2002 | Cunningham et al. |
| 6,362,484 B1 | 3/2002 | Beyne et al. |
| 6,373,869 B1 | 4/2002 | Jacob |
| 6,403,963 B1 | 6/2002 | Nikzad et al. |
| 6,429,943 B1 | 8/2002 | Opsal et al. |
| 6,456,318 B1 | 9/2002 | Noguchi |
| 6,535,531 B1 | 3/2003 | Smith et al. |
| 6,545,281 B1 | 4/2003 | McGregor et al. |
| 6,608,676 B1 | 8/2003 | Zhao et al. |
| 6,711,283 B1 | 3/2004 | Soenksen |
| 6,837,766 B2 | 1/2005 | Costello |
| 7,005,637 B2 | 2/2006 | Costello et al. |
| 7,039,157 B2 | 5/2006 | Fujii et al. |
| 7,046,283 B1 | 5/2006 | Kamasz et al. |
| 7,126,699 B1 | 10/2006 | Wihl et al. |
| 7,130,039 B2 | 10/2006 | Vaez-Iravani et al. |
| 7,136,159 B2 | 11/2006 | Tsai et al. |
| 7,141,791 B2 | 11/2006 | Masnaghetti et al. |
| 7,227,984 B2 | 6/2007 | Cavan |
| 7,233,350 B2 | 6/2007 | Tay |
| 7,283,166 B1 | 10/2007 | Billman |
| 7,321,468 B2 | 1/2008 | Herkommer et al. |
| 7,345,825 B2 | 3/2008 | Chuang et al. |
| 7,352,457 B2 | 4/2008 | Kvamme et al. |
| 7,432,517 B2 | 10/2008 | Botma et al. |
| 7,446,474 B2 | 11/2008 | Maldonado et al. |
| 7,465,935 B2 | 12/2008 | Urano et al. |
| 7,525,649 B1 | 4/2009 | Leong et al. |
| 7,528,943 B2 | 5/2009 | Brown et al. |
| 7,586,108 B2 | 9/2009 | Nihtianov et al. |
| 7,609,309 B2 | 10/2009 | Brown et al. |
| 7,714,287 B1 | 5/2010 | James et al. |
| 7,741,666 B2 | 6/2010 | Nozaki et al. |
| 7,750,280 B2 | 7/2010 | Hwang et al. |
| 7,791,170 B2 | 9/2010 | Chiang et al. |
| 7,800,040 B2 | 9/2010 | Blacksberg et al. |
| 7,813,406 B1 | 10/2010 | Nguyen et al. |
| 7,838,833 B1 | 11/2010 | Lent et al. |
| 7,875,948 B2 | 1/2011 | Hynecek et al. |
| 7,928,382 B2 | 4/2011 | Hatakeyama et al. |
| 7,952,633 B2 | 5/2011 | Brown et al. |
| 7,985,658 B2 | 7/2011 | Lei et al. |
| 8,017,427 B2 | 9/2011 | Manabe |
| 8,138,485 B2 | 3/2012 | Nihtianov et al. |
| 8,309,443 B2 | 11/2012 | Tanaka et al. |
| 8,450,820 B2 | 5/2013 | Nanver et al. |
| 8,455,971 B2 | 6/2013 | Chen et al. |
| 8,513,587 B2 | 8/2013 | Wang et al. |
| 8,514,587 B2 | 8/2013 | Zhang et al. |
| 8,629,384 B1 | 1/2014 | Biellak et al. |
| 8,686,331 B2 | 4/2014 | Armstrong |
| 8,754,972 B2 | 6/2014 | Brown et al. |
| 8,755,417 B1 | 6/2014 | Dribinski |
| 8,873,596 B2 | 10/2014 | Dribinski et al. |
| 8,929,406 B2 | 1/2015 | Chuang et al. |
| 9,426,400 B2 | 8/2016 | Brown et al. |
| 9,478,402 B2 | 10/2016 | Chuang et al. |
| 9,496,425 B2 | 11/2016 | Chern et al. |
| 9,529,182 B2 | 12/2016 | Chuang et al. |
| 9,608,399 B2 | 3/2017 | Chuang et al. |
| 9,860,466 B2 * | 1/2018 | Chuang ............... H04N 5/3722 |
| 2001/0012069 A1 | 8/2001 | Derndinger et al. |
| 2001/0017344 A1 | 8/2001 | Aebi |
| 2001/0024684 A1 | 9/2001 | Steiner et al. |
| 2001/0055424 A1 | 12/2001 | Publicover |
| 2002/0140654 A1 | 10/2002 | Kim et al. |
| 2003/0111707 A1 | 6/2003 | Takaura et al. |
| 2003/0222579 A1 | 12/2003 | Habib et al. |
| 2004/0012684 A1 | 1/2004 | Tinnerino |
| 2004/0021061 A1 | 2/2004 | Bijkerk |
| 2004/0032628 A1 | 2/2004 | Sato et al. |
| 2004/0056279 A1 | 3/2004 | Niigaki et al. |
| 2004/0074261 A1 | 4/2004 | Caron et al. |
| 2004/0175028 A1 | 9/2004 | Cavan |
| 2004/0212708 A1 | 10/2004 | Spartiotis et al. |
| 2004/0217294 A1 | 11/2004 | Zur |
| 2004/0227070 A1 | 11/2004 | Bateman et al. |
| 2005/0122021 A1 | 6/2005 | Smith et al. |
| 2005/0167575 A1 | 8/2005 | Benz et al. |
| 2005/0168602 A1 | 8/2005 | Sumi et al. |
| 2005/0196059 A1 | 9/2005 | Inoue et al. |
| 2005/0264148 A1 | 12/2005 | Maldonado et al. |
| 2005/0287479 A1 | 12/2005 | Moon et al. |

(56) References Cited

U.S. PATENT DOCUMENTS

| | | |
|---|---|---|
| 2006/0054778 A1 | 3/2006 | Suhling |
| 2006/0055321 A1 | 3/2006 | Maldonado et al. |
| 2006/0069460 A1 | 3/2006 | Smith et al. |
| 2006/0087649 A1 | 4/2006 | Ogawa et al. |
| 2006/0103725 A1 | 5/2006 | Brown et al. |
| 2006/0170324 A1 | 8/2006 | Machuca et al. |
| 2006/0188869 A1 | 8/2006 | Zeskind et al. |
| 2007/0002465 A1 | 1/2007 | Chuang et al. |
| 2007/0007429 A1 | 1/2007 | Fairley et al. |
| 2007/0023770 A1 | 2/2007 | Miyajima et al. |
| 2007/0034987 A1 | 2/2007 | Costello et al. |
| 2007/0064135 A1 | 3/2007 | Brown et al. |
| 2007/0072326 A1 | 3/2007 | Zheng et al. |
| 2007/0096648 A1 | 5/2007 | Nakajima et al. |
| 2007/0103769 A1 | 5/2007 | Kuwabara |
| 2007/0138378 A1 | 6/2007 | Chang et al. |
| 2007/0146693 A1 | 6/2007 | Brown et al. |
| 2007/0171298 A1 | 7/2007 | Kurane |
| 2007/0177289 A1 | 8/2007 | Shim et al. |
| 2007/0188744 A1 | 8/2007 | Leslie et al. |
| 2007/0210395 A1 | 9/2007 | Maruyama et al. |
| 2007/0229677 A1 | 10/2007 | Mochizuki et al. |
| 2007/0291810 A1 | 12/2007 | Luo et al. |
| 2008/0002037 A1 | 1/2008 | Ueda |
| 2008/0044932 A1 | 2/2008 | Samoilov et al. |
| 2008/0068593 A1 | 3/2008 | Nakano et al. |
| 2008/0074513 A1 | 3/2008 | Noguchi |
| 2008/0079830 A1 | 4/2008 | Lepage |
| 2008/0173903 A1 | 7/2008 | Imai et al. |
| 2008/0232674 A1 | 9/2008 | Sakai et al. |
| 2008/0278775 A1 | 11/2008 | Katzir et al. |
| 2008/0315092 A1 | 12/2008 | Kley |
| 2008/0315121 A1 | 12/2008 | Nihtianov et al. |
| 2009/0009645 A1 | 1/2009 | Schrey et al. |
| 2009/0021717 A1 | 1/2009 | Nihtianov et al. |
| 2009/0079973 A1 | 3/2009 | Uto et al. |
| 2009/0080759 A1 | 3/2009 | Bhaskar et al. |
| 2009/0091752 A1 | 4/2009 | Terasawa et al. |
| 2009/0108207 A1 | 4/2009 | Liu |
| 2009/0125242 A1 | 5/2009 | Choi et al. |
| 2009/0128912 A1 | 5/2009 | Okada et al. |
| 2009/0147255 A1 | 6/2009 | Erington et al. |
| 2009/0168152 A1 | 7/2009 | Gelernt et al. |
| 2009/0180176 A1 | 7/2009 | Armstrong et al. |
| 2010/0026865 A1 | 2/2010 | Tivarus et al. |
| 2010/0038540 A1 | 2/2010 | Hannebauer |
| 2010/0102213 A1 | 4/2010 | Garris |
| 2010/0103409 A1 | 4/2010 | Ohshima et al. |
| 2010/0104173 A1 | 4/2010 | Yoshida et al. |
| 2010/0148667 A1 | 6/2010 | Niigaki et al. |
| 2010/0188655 A1 | 7/2010 | Brown et al. |
| 2010/0208979 A1 | 8/2010 | Abbott et al. |
| 2010/0309308 A1 | 12/2010 | Saphier et al. |
| 2011/0019044 A1 | 1/2011 | Wang et al. |
| 2011/0073982 A1 | 3/2011 | Armstrong et al. |
| 2011/0101219 A1 | 5/2011 | Uchiyama et al. |
| 2011/0116077 A1 | 5/2011 | Chuang et al. |
| 2011/0168886 A1 | 7/2011 | Shadman et al. |
| 2011/0169116 A1 | 7/2011 | Nanver et al. |
| 2011/0234790 A1 | 9/2011 | True |
| 2011/0256655 A1 | 10/2011 | Nikzad et al. |
| 2011/0261354 A1 | 10/2011 | Sinfield et al. |
| 2011/0279725 A1 | 11/2011 | Cazaux et al. |
| 2011/0291109 A1 | 12/2011 | Wraback et al. |
| 2012/0012811 A1 | 1/2012 | Deflumere et al. |
| 2012/0012957 A1 | 1/2012 | Larsen et al. |
| 2012/0081684 A1 | 4/2012 | Den et al. |
| 2012/0132823 A1 | 5/2012 | Menge et al. |
| 2012/0160993 A1 | 6/2012 | Nevet et al. |
| 2012/0170021 A1 | 7/2012 | Walsh |
| 2012/0228485 A1 | 9/2012 | Iwakiri et al. |
| 2012/0268722 A1 | 10/2012 | Nihtianov et al. |
| 2013/0009069 A1 | 1/2013 | Okada |
| 2013/0016346 A1 | 1/2013 | Romanovsky et al. |
| 2013/0017205 A1 | 1/2013 | Giaccia et al. |
| 2013/0020491 A1 | 1/2013 | Mazzillo |
| 2013/0056843 A1 | 3/2013 | Lee et al. |
| 2013/0077086 A1 | 3/2013 | Chuang et al. |
| 2013/0082241 A1 | 4/2013 | Kub et al. |
| 2013/0088706 A1 | 4/2013 | Chuang et al. |
| 2013/0114085 A1 | 5/2013 | Wang et al. |
| 2013/0126705 A1 | 5/2013 | Maleev |
| 2013/0148112 A1 | 6/2013 | Chuang et al. |
| 2013/0169957 A1 | 7/2013 | Wolf et al. |
| 2013/0176552 A1 | 7/2013 | Brown et al. |
| 2013/0270663 A1 | 10/2013 | Lin et al. |
| 2013/0313440 A1 | 11/2013 | Chuang et al. |
| 2013/0320211 A1 | 12/2013 | Park et al. |
| 2013/0336574 A1 | 12/2013 | Nasser-Ghodsi et al. |
| 2013/0341504 A1 | 12/2013 | Neill et al. |
| 2014/0151552 A1 | 6/2014 | Jiang et al. |
| 2014/0203386 A1 | 7/2014 | Bui et al. |
| 2014/0246595 A1 | 9/2014 | Menge et al. |
| 2014/0305367 A1 | 10/2014 | Chuang et al. |
| 2014/0362203 A1 | 12/2014 | Delaney et al. |
| 2015/0007765 A1 | 1/2015 | Dribinski |
| 2015/0294998 A1 | 10/2015 | Nihtianov et al. |
| 2015/0369750 A1 | 12/2015 | Wang et al. |

FOREIGN PATENT DOCUMENTS

| | | |
|---|---|---|
| EP | 0746871 A1 | 12/1996 |
| EP | 1538827 A1 | 6/2005 |
| EP | 1939917 A2 | 7/2008 |
| EP | 2088763 A2 | 8/2009 |
| EP | 2346094 A1 | 7/2011 |
| JP | H08241977 A | 9/1996 |
| JP | H10171965 A | 6/1998 |
| JP | H11153516 A | 6/1999 |
| JP | 2002033473 | 1/2002 |
| JP | 2004031452 A | 1/2004 |
| JP | 2007086108 A | 4/2007 |
| JP | 2008096430 A | 4/2008 |
| JP | 2008224303 A | 9/2008 |
| JP | 2009117454 A | 5/2009 |
| JP | 5304674 B2 | 10/2013 |
| KR | 20020084541 A | 11/2002 |
| KR | 100688497 B1 | 3/2007 |
| KR | 100826407 B1 | 5/2008 |
| RU | 2297070 C2 | 4/2007 |
| WO | 9532518 A1 | 11/1995 |
| WO | 9600381 A1 | 1/1996 |
| WO | 9617372 A1 | 6/1996 |
| WO | 2007035858 A2 | 3/2007 |
| WO | 2011091159 A1 | 7/2011 |
| WO | 2014067754 A2 | 5/2014 |

OTHER PUBLICATIONS

Allen et al., Work Function, Photoelectric Threshold, and Surface . . . ; Physical Review, vol. 127, No. 1, Jul. 1, 1962, pp. 150-158.

Fanton et al, Multiparameter Measurements of Thin Film . . . , Journal of Applied Physics, vol. 73, No. 11, p. 7035 (1993).

Fu et al., Optimizing GaN photocathode structure for higher . . . ; Optik, vol. 123, No. 9, May 2012, pp. 756-768.

Hecht, Optics, Fourth Edition, India: Pearson Education Pte, Ltd. 2004.

Hecht, Optics, Second Edition, Adelphi University, 1987, Addison-Wesley Publishing Company, Inc., 3 pages.

Henderson, Brian S., Study of Negative Electron Affinity . . . , Dept. of Physics, Rice Univ., Aug. 7, 2009, 18 pgs.

Howorth et al., Transmission silicon photoemitters . . . , Jrnl of Physics D: Applied Physics, vol. 9, No. 5, Apr. 1, 1976, pp. 785-794.

ISR and Written Opinion dated Mar. 31, 2014 for PCT/US2013/074124.

Janesick, James R., Scientific Charge—Coupled Devices, SPIE Press, 2001, pp. 556-561.

Kla-Tencorcoporation, filed application U.S. Appl. No. 62/059,368, filed Oct. 3, 2014 and entitled "183nm Laser and Inspection System".

Leng et al, Simultaneous Measurement of Six Layers . . . , Journal of Applied Physics, vol. 81, No. 8, p. 3570 (1997).

(56) References Cited

OTHER PUBLICATIONS

Martinelli, Ramon U., Infrared Photoemission from Silicon, Applied Physics Letters, vol. 16, No. 7, Apr. 1, 1970, pp. 261-262.

Martinelli, Ramon U., Reflection and Transmission Secondary Emission . . . , Applied Physics Letters, vol. 17, No. 8, Oct. 15, 1970, pp. 313-314.

Mouchart et al., Thin Film Optical Coatings. 7: Two Layer Coatings Close to Antireflection, Applied Optics, vol. 18, No. 8, Apr. 15, 1979, pp. 1226-1232.

Nanver et al., Pure-Boron Chemical-Vapor-Deposited Layers: a New Material for Silicon Device Processing, 18th IEEE International Conference on Advanced Thermal Processing of Semiconductors (RTP), Sep. 28, 2010-Oct. 1, 2010, pp. 136-139.

Nanver, Silicon Photodiodes for Low Penetration Depth Beams such as DUV/VUV/EUV Lightand Low-Energy Electrons, Advances in Photodiodes, G. Betta, ed., Mar. 22, 2011, pp. 205-224, www.intechopen.com.

Raoult, Efficient generation of narrow-bandwidth . . . , Jul. 15, 1998, vol. 23, No. 14, Optics Letters, pp. 1117-1119.

Sarubbi et al., Chemical Vapor Deposition of α-Boron Layers on Silicon for Controlled Nanometer-Deep p+ n Junction Formation, J. Electron. Mat., vol. 39, No. 2, Feb. 2010, pp. 162-173.

Sarubbi et al., Pure boron-doped photodiodes . . . IEEE, Sep. 15, 2008, pp. 278-281.

Sobieski, Stanley, Intensified Charge Coupled Devices for Ultra Low Light Level Imaging, NASA, Goddard Space Flight Center, SPIE vol. 78 (1976) Low Light Level Devices, pp. 73-77.

Tobin, Kenneth W., Inspection in Semiconductor Manufacturing, Webster's Encyclopedia of Electrical and Electronic Engineering, vol. 10, pp. 242-262, Wiley & Sons, NY, NY, 1999.

Xiaogian, Fu, Higher Quantum Efficiency by Optimizing . . . 978-1-4244-6644-3/10 IEEE, pp. 234-235.

\* cited by examiner

SENSOR WITH ELECTRICALLY CONTROLLABLE APERTURE FOR INSPECTION AND METROLOGY SYSTEMS

RELATED APPLICATIONS

The present application is a continuation of U.S. patent application Ser. No. 15/153,543, filed May 12, 2016, which claims priority to U.S. Provisional Application Ser. No. 62/161,450, filed May 14, 2015 and U.S. Provisional Application Ser. No. 62/172,242, filed Jun. 8, 2015, which are incorporated herein by reference.

The present application is related to co-owned and co-pending U.S. patent application Ser. No. 14/691,966 (Published Application No. 2015/0369750), filed Apr. 21, 2015, entitled "CONFOCAL LINE INSPECTION OPTICAL SYSTEM", and to U.S. patent application Ser. No. 11/805,907 (Published Application No. 2011/0073982), entitled "INSPECTION SYSTEM USING BACK SIDE ILLUMINATED LINEAR SENSOR", filed on May 25, 2007, which are incorporated herein by reference.

BACKGROUND OF THE DISCLOSURE

Field of the Disclosure

The present application relates to line sensors and associated electronic circuits suitable for sensing radiation at visible, UV, deep UV (DUV), vacuum UV (VUV), extreme UV (EUV) and X-ray wavelengths, and for sensing electrons or other charged particles, and to methods for operating such line sensors. The sensors and circuits are particularly suitable for use in inspection and metrology systems, including those used to inspect and/or measure features on photomasks, reticles, and semiconductor wafers.

Related Art

The integrated circuit industry requires inspection tools with increasingly higher sensitivity to detect ever smaller defects and particles, and requires high precision metrology tools for accurately measuring the dimensions of small features on semiconductor wafers. The semiconductor industry is currently manufacturing semiconductor device with feature dimensions around 20 nm and smaller. Within a few years, the industry will be manufacturing devices with feature dimensions around 5 nm. Particles and defects just a few nm in size can reduce wafer yields, and changes in feature dimensions of a few tenths of 1 nm or less can cause a significant change in the electrical performance, or failure, of a transistor or memory device.

Semiconductor inspection and metrology tools are most useful if they can inspect or measure on all, or most, of the different materials and structures used in CMOS manufacturing. Different materials and structures have very different reflectivities from one another. In order to have the flexibility semiconductor inspection and metrology tools may use multiple wavelengths and/or multiple angles of light illumination and light collection. Selecting which angles to use typically involves switching appropriately shaped and sized apertures into the right location in the optical path according to what is being inspected or measured.

Various inspection and metrology tools of the type related to the present invention are disclosed, for example, in U.S. patent application Ser. No. 14/273,424, entitled "A Low-Noise Sensor And An Inspection System Using A Low-Noise Sensor", and filed on May 8, 2014, U.S. patent application Ser. No. 13/364,308, entitled "High-density digitizer", filed on Feb. 1, 2012, U.S. patent application Ser. No. 14/096,911, entitled "Method and apparatus for high speed acquisition of moving images using pulsed illumination", filed on Dec. 4, 2013, U.S. patent application Ser. No. 13/710,315, entitled "Electron-bombarded charge-coupled device and inspection systems using EBCCD detectors", filed on Dec. 10, 2012, U.S. patent application Ser. No. 13/792,166, entitled "Back-illuminated sensor with boron layer", filed on Mar. 10, 2013, U.S. patent application Ser. No. 13/947,975, entitled "Photocathode including silicon substrate with boron layer", filed on Jul. 22, 2013, U.S. Published Patent Application 2010/0188655, entitled, "TDI sensor modules with localized driving and signal processing circuitry for high speed inspection", filed on Oct. 7, 2009, U.S. Published Patent Application 2010/0301437, entitled "Anti-reflective coating for sensors suitable for high throughput inspection systems", filed on Jun. 1, 2009, U.S. Pat. No. 7,609,309, entitled "Continuous clocking of TDI sensors", issued on Oct. 27, 2009, and U.S. Pat. No. 7,952,633, entitled "Apparatus for continuous clocking of TDI sensors", issued on May 31, 2011. These applications and patents are incorporated by reference herein.

Apertures are mechanical devices that can occupy significant space. Mechanical motion of apertures can take tens or hundreds of milliseconds, thus slowing inspections or measurements that require data to be collected with more than one aperture. Adding or replacing apertures on an existing inspection or metrology system in order to provide new or improved capability can be difficult owing to space constraints.

Therefore, a need arises for linear sensors having adjustable apertures that facilitate quickly and reliably adjusting the size of each pixel's light sensitive region during operation of an existing inspection or metrology system in a way that overcomes some, or all, of the above-mentioned disadvantages associated with conventional approaches.

SUMMARY OF THE DISCLOSURE

The present invention is directed to electrically controlling the pixel aperture size in a linear sensor by way of generating a non-monotonic voltage profile that controllably adjusts (reduces or expands) the effective light sensitive region from which photoelectrons are collected for measurement by each pixel. Each pixel includes an elongated resistive control gate, and each pixel's maximum light sensitive region is defined by a portion of the semiconductor substrate disposed under (adjacent to) the pixel's resistive control gate. Similar to conventional sensors, control voltages respectively applied by way of end electrodes to opposing end portions of each pixel's resistive control gate produce an associated electric field in the pixel's light sensitive region, whereby photoelectrons generated by incident light entering the pixel's light sensitive region are driven by the associated electric field to one or more charge accumulation regions. According to the present invention, one or more centrally located aperture control electrodes are disposed across each pixel's resistive control gate between the two resistive control gate end portions, and an associated control circuit is configured to selectively generate a non-monotonic (e.g., two-part) voltage profile by way of applying a more negative control voltage to a selected central electrode than that applied to the two end electrodes. That is, the non-monotonic voltage profile generates an electric field in the pixel such that photoelectrons generated in a first portion of the pixel's light sensitive region that is located on a first side of the central aperture control electrode are driven toward a first end of the resistive control gate, and photoelectrons generated in a second portion of the pixel's light sensitive region on a second side of the central aperture control electrode are driven toward the opposite (second) end of the resistive control gate. The effective size of each pixel's light sensitive region is thereby controllably adjusted to include only the first portion of the pixel's light sensitive region by way of generating the non-monotonic voltage profile and subsequently measuring the photoelectron charge collected only from the first end of the resistive control gate.

A method of inspecting or measuring a sample at high speed is also described. This method includes directing and focusing radiation onto the sample, and receiving radiation from the sample and directing received radiation to a line sensor. The received radiation may be scattered radiation or reflected radiation. The line sensor incorporates a resistive control gate having a potential gradient generated across its length by way of electrodes, whereby the resistive control gate generates an electric field that directs photoelectrons in the sensor to one or more accumulation regions. A control circuit is configured to apply more negative voltages to one or more centrally located electrodes and more positive voltages to electrodes disposed at end portions of the resistive control gate, thereby generating electric fields that bias (drive) photoelectrons generated in one region of the sensor to an accumulation region while preventing other photoelectrons generated in other regions of the sensor from reaching the accumulation region.

The method of inspecting can further include setting voltages on the electrodes attached to the resistive gate according to the inspection or measurement being made. In one embodiment the voltages may be changed during the inspection or measurement to optimize the light collection process, or may be used to adjust the effective aperture size of each individual pixel during a pre-inspection calibration period to such that all pixels of the sensor have a uniform aperture size.

A system for inspecting a sample is also described. This system includes an illumination source, a device configured to perform light detection, optics configured to direct light from the illumination source to the sample and to direct light outputs or reflections from the sample to the device, and a driving circuit. The line sensor incorporates a resistive gate with a potential gradient across it that directs photoelectrons in the sensor to an accumulation region. The line sensor includes multiple electrodes attached to the resistive gate allowing the potential gradient to be adjusted so as to direct photoelectrons from one region of the sensor to an accumulation region while preventing other photoelectrons from reaching the accumulation region. The driving circuit sets voltages on one or more of the multiple electrodes in order to control from which regions of the sensor photoelectrons are directed to the accumulation region.

In one embodiment, the line sensor may further comprise a semiconductor membrane. In another embodiment, the semiconductor membrane may include circuit elements formed on a first surface of the semiconductor membrane and a pure boron layer deposited on a second surface of the semiconductor membrane. In yet another embodiment, the line sensor may comprise an electron bombarded line sensor. In yet another embodiment, the system may include multiple line sensors. In yet another embodiment, the line sensor may include an optical knife edge or other mechanical aperture structure, and the electrical aperture adjustment maybe utilized to correct for misalignment of the mechanical aperture structure, thereby simplifying alignment and reducing manufacturing costs. In yet another embodiment, the knife edge or other mechanical aperture is movable under computer control, so that the computer can select different inspection modes by appropriate positioning of the knife edge or aperture in combination with setting voltages on the electrodes on the resistive gate of the line sensor.

The sample may be supported by a stage, which moves relative to the optics during the inspection. The electrical charges may be read out from the sensor in synchrony with the motion of the stage.

The exemplary inspection system may include one or more illumination paths that illuminate the sample from different angles of incidence and/or different azimuth angles and/or with different wavelengths and/or polarization states. The exemplary inspection system may include one or more collection paths that collect light reflected or scattered by the sample in different directions and/or are sensitive to different wavelengths and/or to different polarization states.

DETAILED DESCRIPTION OF THE DRAWINGS

Improved sensors for semiconductor inspection and metrology systems are described herein. The following description is presented to enable one of ordinary skill in the art to make and use the invention as provided in the context of a particular application and its requirements. As used herein, directional terms such as "top", "bottom", "over", "under", "upper", "upward", "lower", "down", and "downward" are intended to provide relative positions for purposes of description, and are not intended to designate an absolute frame of reference. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 1:
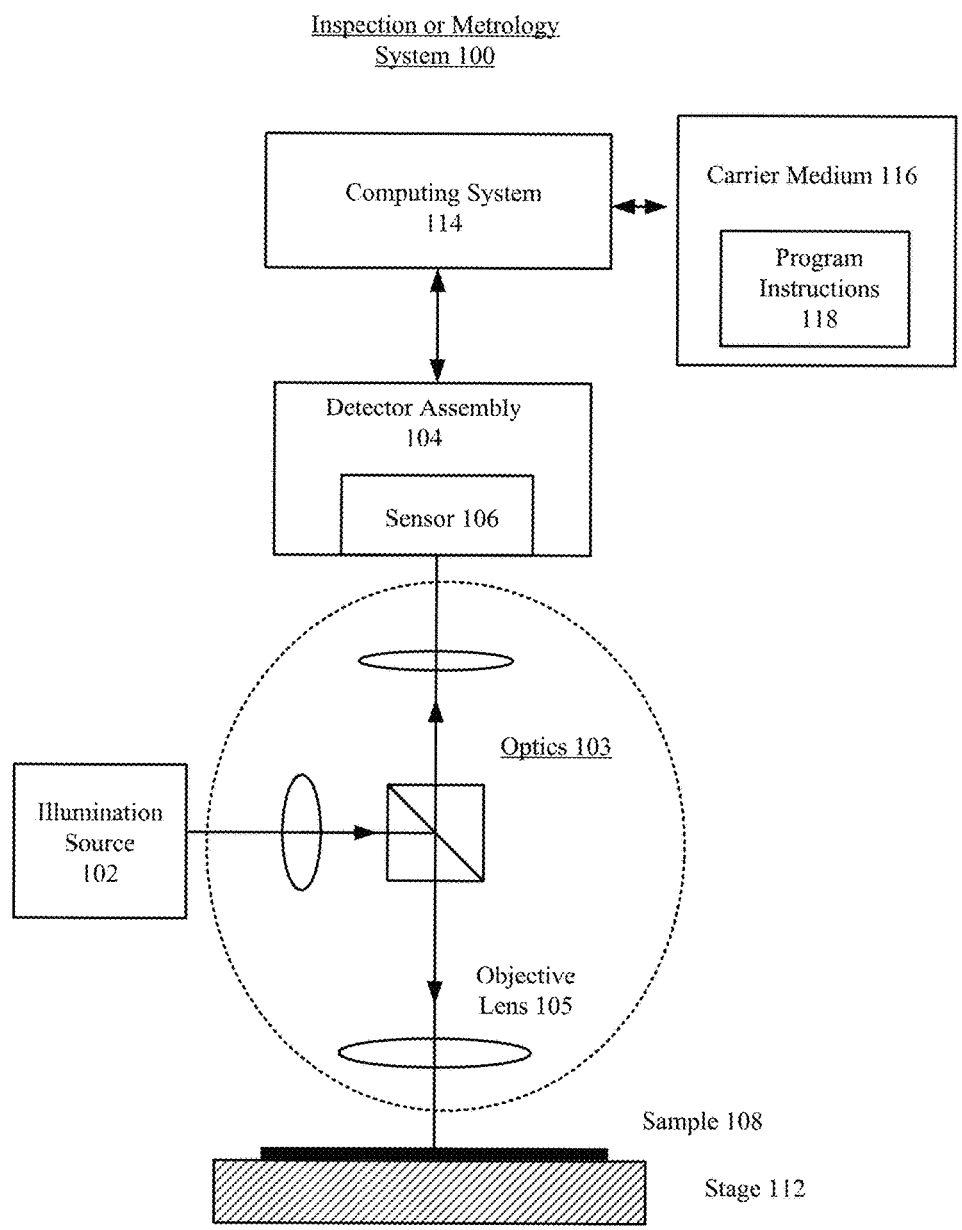
FIG. 1 illustrates an exemplary inspection or metrology system.

FIG. 1 illustrates an exemplary inspection or metrology system 100 configured to inspect or measure a sample 108, such as a wafer, reticle, or photomask. Sample 108 is placed on a stage 112 to facilitate movement to different regions of sample 108 underneath the optics. Stage 112 may comprise an X-Y stage or an R-θ stage. In some embodiments, stage 112 can adjust the height of sample 108 during inspection to maintain focus. In other embodiments, an objective lens 105 can be adjusted to maintain focus.

An illumination source 102 may comprise one or more lasers and/or a broad-band light source. Illumination source 102 may emit DUV and/or VUV radiation. Optics 103, including an objective lens 105, directs that radiation towards and focuses it on sample 108. Optics 103 may also comprise mirrors, lenses, polarizers and/or beam splitters (not shown for simplicity). Light reflected or scattered from sample 108 is collected, directed, and focused by optics 103 onto a sensor 106, which is within a detector assembly 104.

Detector assembly 104 includes at least one of the sensors described herein. In one embodiment, the output of sensor 106 is provided to a computing system 114, which analyzes the output. Computing system 114 is configured by program instructions 118, which can be stored on a carrier medium 116. In one embodiment computing system 114 controls the inspection or metrology system 100 and sensor 106 to inspect or measure a structure on sample 108 in accordance with a method disclosed herein.

In one embodiment, illumination source 102 may be a continuous source, such as an arc lamp, a laser-pumped plasma light source, or a CW laser. In another embodiment, illumination source 102 may be a pulsed source, such as a mode-locked laser, a Q-switched laser, or a plasma light source pumped by a Q-switched laser. In one embodiment of inspection or metrology system 100 incorporating a Q-switched laser, the line sensor or sensors within detector assembly 104 are synchronized with the laser pulses.

One embodiment of inspection or metrology system 100 illuminates a line on sample 108, and collects scattered and/or reflected light in one or more dark-field and/or bright-field collection channels. In this embodiment, detector assembly 104 may include a line sensor or an electron-bombarded line sensor. For example, in this embodiment of system 100, the resistive gate structure described herein may be used to select portions of the scattered and/or reflected light to collect.

Additional details of various embodiments of inspection or metrology system 100 are described in U.S. patent application Ser. No. 13/554,954, entitled "Wafer inspection system", filed on Jul. 9, 2012, U.S. Published Patent Application 2009/0180176, entitled "Split field inspection system using small catadioptric objectives", published on Jul. 16, 2009, U.S. Published Patent Application 2007/0002465, entitled "Beam delivery system for laser dark-field illumination in a catadioptric optical system", published on Jan. 4, 2007, U.S. Pat. No. 5,999,310, entitled "Ultra-broadband UV microscope imaging system with wide range zoom capability", issued on Dec. 7, 1999, U.S. Pat. No. 7,525,649, entitled "Surface inspection system using laser line illumination with two dimensional imaging", issued on Apr. 28, 2009, U.S. Published Patent Application 2013/0114085, entitled "Dynamically Adjustable Semiconductor Metrology System", by Wang et al. and published on May 9, 2013, U.S. Pat. No. 5,608,526, entitled "Focused Beam Spectroscopic Ellipsometry Method and System", by Piwonka-Corle et al., issued on Mar. 4, 1997, and U.S. Pat. No. 6,297,880, entitled "Apparatus for Analysing Multi-Layer Thin Film Stacks on Semiconductors", by Rosencwaig et al., issued on Oct. 2, 2001. All of these patents and patent applications are incorporated by reference herein.

Figure 2A:
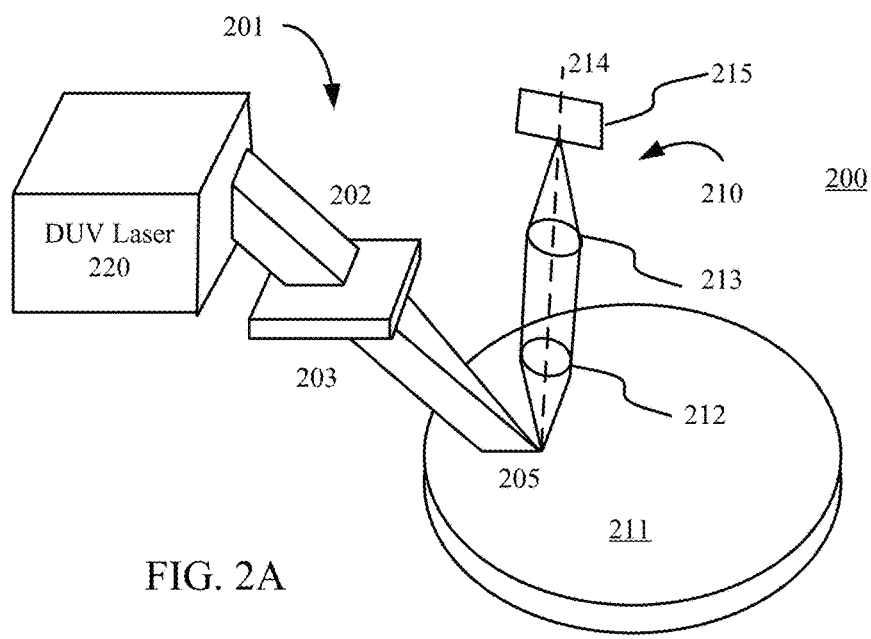
FIGS. 2A and 2B illustrates an exemplary inspection system with line illumination and one or more collection channels.
Figure 2B:
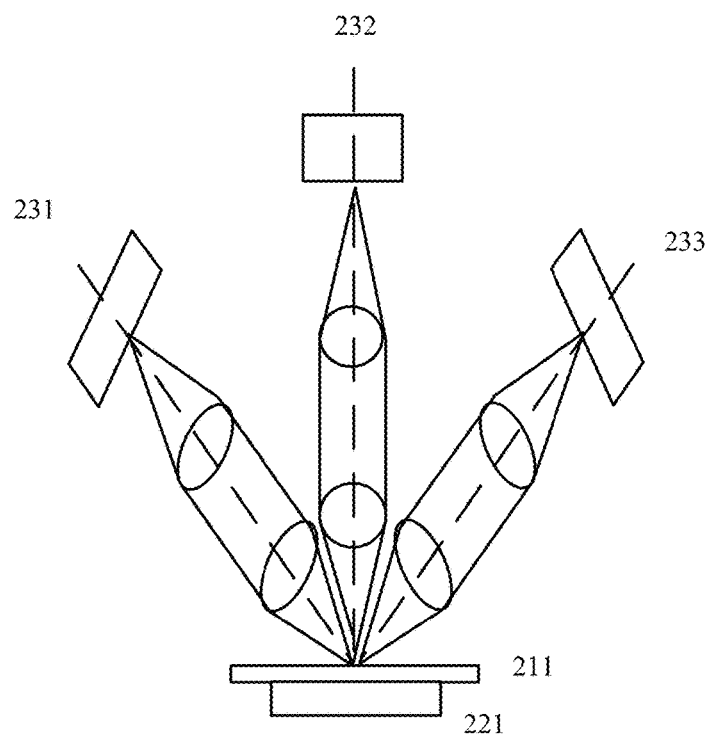

FIGS. 2A and 2B illustrate aspects of dark-field inspection systems that incorporate sensors and/or methods described herein in accordance with other exemplary embodiments of the present invention. In FIG. 2A, illumination optics 201 comprises a laser system 220, which generates light 202 that is focused by a mirror or lens 203 into a line 205 on surface of a wafer or photomask (sample) 211 being inspected. Collection optics 210 directs light scattered from line 205 to a sensor 215 using lenses and/or mirrors 212 and 213. An optical axis 214 of collection optics 210 is not in the illumination plane of line 205. In some embodiments, optical axis 214 is approximately perpendicular to line 205. Sensor 215 comprises an array sensor, such as a linear array sensor. Sensor 215 may comprise a sensor as described herein, and/or one of the methods described herein may be used to inspect sample 211.

FIG. 2B illustrates one embodiment of multiple dark-field collection systems 231, 232 and 233, each collection system substantially similar to collection optics 210 of FIG. 2A. Collection systems 231, 232 and 233 may be used in combination with illumination optics substantially similar to illumination optics 201 of FIG. 2A. Each collection system 231, 232 and 233 incorporates one, or more, of the sensors described herein. Sample 211 is supported on stage 221, which moves the areas to be inspected underneath the optics. Stage 221 may comprise an X-Y stage or an R-θ stage, which preferably moves substantially continuously during the inspection to inspect large areas of the sample with minimal dead time.

More details of inspection systems in accordance with the embodiments illustrated in FIGS. 2A and 2B are described in above cited, co-pending U.S. patent application Ser. No. 14/691,966, entitled "Confocal Line Inspection Optical System", filed by Wang et al. on Apr. 21, 2015, U.S. Pat. No. 7,525,649, entitled "Surface inspection system using laser line illumination with two dimensional imaging", issued on Apr. 28, 2009, and U.S. Pat. No. 6,608,676, entitled "System for detecting anomalies and/or features of a surface", issued on Aug. 19, 2003. All of these patents and patent applications are incorporated by reference herein.

Figure 3A:
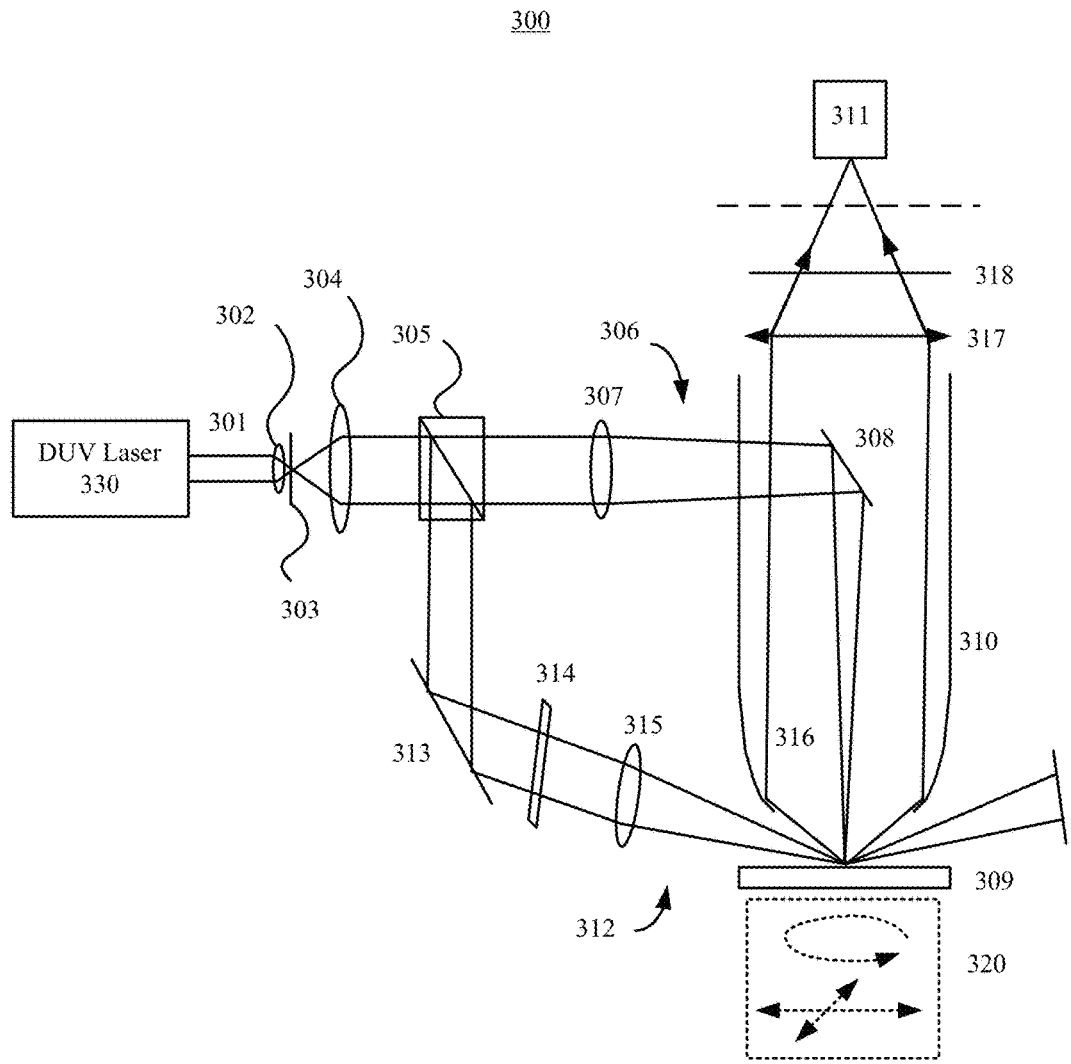
FIG. 3A illustrates an exemplary inspection system with normal and oblique illumination.

FIG. 3A illustrates an inspection system 300 configured to detect particles or defects on a sample using both normal and oblique illumination beams. In this configuration, a laser system 330 provides a laser beam 301. A lens 302 focuses beam 301 through a spatial filter 303. Lens 304 collimates the beam and conveys it to a polarizing beam splitter 305. Beam splitter 305 passes a first polarized component to the normal illumination channel and a second polarized component to the oblique illumination channel, where the first and second components are orthogonal. In a normal illumination channel 306, the first polarized component is focused by optics 307 and reflected by a mirror 308 towards a surface of a sample 309. The radiation scattered by sample 309 (such as a wafer or photomask) is collected and focused by a paraboloidal mirror 310 to a sensor 311.

In an oblique illumination channel 312, the second polarized component is reflected by a beam splitter 305 to a mirror 313 which reflects such beam through a half-wave plate 314 and focused by optics 315 to sample 309. Radiation originating from the oblique illumination beam in oblique channel 312 and scattered by sample 309 is collected by paraboloidal mirror 310 and focused to sensor 311. Sensor 311 and the illuminated area (from the normal and oblique illumination channels on sample 309) are preferably at the foci of paraboloidal mirror 310.

Paraboloidal mirror 310 collimates the scattered radiation from sample 309 into a collimated beam 316. Collimated beam 316 is then focused by an objective 317 and through an analyzer 318 to sensor 311. Note that curved mirrored surfaces having shapes other than paraboloidal shapes may also be used. An instrument 320 can provide relative motion between the beams and sample 309 so that spots are scanned across the surface of sample 309. Sensor 311 may comprise one or more of the sensors described herein. U.S. Pat. No. 6,201,601, entitled "Sample inspection system", issued on Mar. 13, 2001, and U.S. Published Patent Application 2013/16346, entitled "Wafer Inspection", filed by Romanovsky et al. describe additional aspects and details of inspection system 300. These documents are incorporated by reference herein.

Figure 3B:
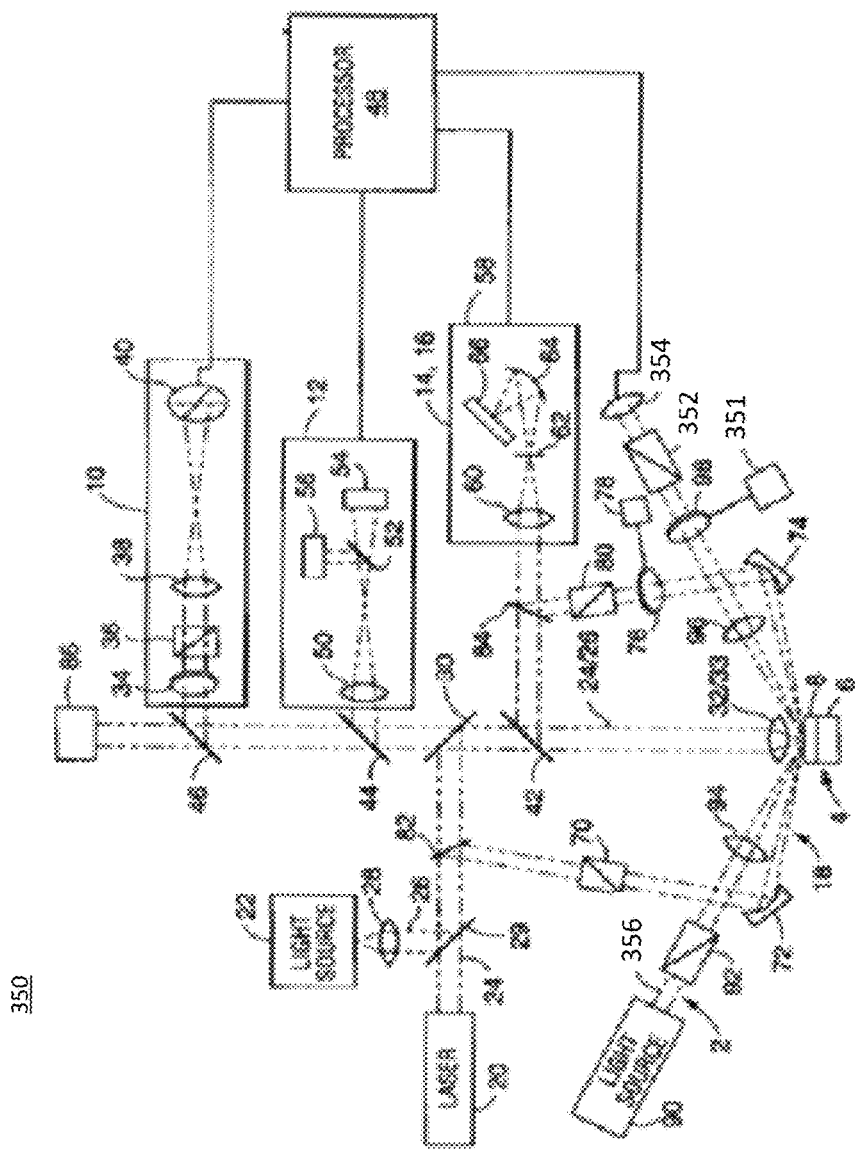
FIG. 3B illustrates an exemplary metrology system with multiple measurement subsystems.

FIG. 3B illustrates an exemplary metrology system 350 with multiple measurement subsystems which incorporates one or more of the sensors disclosed herein. Metrology system 350 includes a Beam Profile Ellipsometer (BPE) 10, a Beam Profile Reflectometer (BPR) 12, a Broadband Reflective Spectrometer (BRS) 14, a Deep Ultra Violet Reflective Spectrometer (DUV) 16, a Broadband Spectroscopic Ellipsometer (BSE) 18, and a reference ellipsometer 2. These six optical measurement devices may utilize as few as three optical sources: lasers 20 and 90, and white light source 22. Laser 20 generates a probe beam 24, and white light source 22 generates probe beam 26 (which is collimated by lens 28 and directed along the same path as probe beam 24 by mirror 29). Laser 20 ideally is a solid state laser diode which emits a linearly polarized 3 mW beam at a visible or near IR wavelength such as a wavelength near 670 nm. White light source 22 is ideally a broad-band, laser-pumped plasma lamp that produces a polychromatic beam that covers a spectrum of about 200 nm to 800 nm or broader. The probe beams 24/26 are reflected by mirror 30, and pass through mirror 42 to sample 4.

The probe beams 24/26 are focused onto the surface of the sample with a lens 32 or lens 33. In the preferred embodiment, two lenses 32/33 are mounted in a turret (not shown) and are alternatively movable into the path of probe beams 24/26. Lens 32 is a microscope objective lens with a high numerical aperture (on the order of 0.90 NA) to create a large spread of angles of incidence with respect to the sample surface, and to create a spot size of about one micron in diameter. Lens 33 is a reflective lens having a lower numerical aperture (on the order of 0.1 to 0.4 NA) and capable of focusing deep UV light to a spot size of about 10-15 microns.

Beam profile ellipsometry (BPE) is discussed in U.S. Pat. No. 5,181,080, issued Jan. 19, 1993, which is incorporated by reference herein. BPE 10 includes a quarter wave plate 34, polarizer 36, lens 38 and a quad detector 40. In operation, linearly polarized probe beam 24 is focused onto sample 4 by lens 32. Light reflected from the sample surface passes up through lens 32, through mirrors 42, 30 and 44, and directed into BPE 10 by mirror 46. The positions of the rays within the reflected probe beam correspond to specific angles of incidence with respect to the sample's surface. Quarter-wave plate 34 retards the phase of one of the polarization states of the beam by 90 degrees. Linear polarizer 36 causes the two polarization states of the beam to interfere with each other. For maximum signal, the axis of the polarizer 36 should be oriented at an angle of 45 degrees with respect to the fast and slow axis of the quarter-wave plate 34. Detector 40 is a quad-cell detector with four radially disposed quadrants that each intercept one quarter of the probe beam and generate a separate output signal proportional to the power of the portion of the probe beam striking that quadrant. The output signals from each quadrant are sent to a processor 48. As discussed in U.S. Pat. No. 5,181,080, by monitoring the change in the polarization state of the beam, ellipsometric information, such as $\Psi$ and $\Delta$, can be determined.

Beam profile reflectometry (BPR) is discussed in U.S. Pat. No. 4,999,014, issued on Mar. 12, 1991, which is incorporated by reference herein. BPR 12 includes a lens 50, beam splitter 52 and two linear detector arrays 54 and 56 to measure the reflectance of the sample. In operation, linearly polarized probe beam 24 is focused onto sample 4 by lens 32, with various rays within the beam striking the sample surface at a range of angles of incidence. Light reflected from the sample surface passes up through lens 32, through mirrors 42 and 30, and directed into BPR 12 by mirror 44. The positions of the rays within the reflected probe beam correspond to specific angles of incidence with respect to the sample's surface. Lens 50 spatially spreads the beam two-dimensionally. Beam splitter 52 separates the s and p components of the beam, and detector arrays 54 and 56 are oriented orthogonal to each other to isolate information about s and p polarized light. The higher angles of incidence rays will fall closer to the opposed ends of the arrays. The output from each element in the detector arrays will correspond to different angles of incidence. Detector arrays 54/56 measure the intensity across the reflected probe beam as a function of the angle of incidence with respect to the sample surface. Detector arrays 54/56 may comprise one or more line sensors with resistive gates as described herein. The processor 48 receives the output of the detector arrays 54/56, and derives the thickness and refractive index of the thin film layer 8 based on these angular dependent intensity measurements by utilizing various types of modeling algorithms. Optimization routines which use iterative processes such as least square fitting routines are typically employed. One example of this type of optimization routine is described in "Multiparameter Measurements of Thin Films Using Beam-Profile Reflectivity," Fanton et al., Journal of Applied Physics, Vol. 73, No. 11, p.7035, 1993. Another example appears in "Simultaneous Measurement of Six Layers in a Silicon on Insulator Film Stack Using Spectrophotometry and Beam Profile Reflectometry," Leng et al., Journal of Applied Physics, Vol. 81, No. 8, page 3570, 1997.

Broadband reflective spectrometer (BRS) 14 simultaneously probes the sample 4 with multiple wavelengths of light. BRS 14 uses lens 32 and includes a broadband spectrometer 58 which can be of any type commonly known and used in the prior art. The spectrometer 58 includes a lens 60, aperture 62, dispersive element 64 and detector array 66. During operation, probe beam 26 from white light source 22 is focused onto sample 4 by lens 32. Light reflected from the surface of the sample passes up through lens 32, and is directed by mirror 42 (through mirror 84) to spectrometer 58. The lens 60 focuses the probe beam through aperture 62, which defines a spot in the field of view on the sample surface to analyze. Dispersive element 64, such as a diffraction grating, prism or holographic plate, angularly disperses the beam as a function of wavelength to individual detector elements contained in the detector array 66. The different detector elements measure the optical intensities of the different wavelengths of light contained in the probe beam, preferably simultaneously. In a preferred embodiment, detector array 66 comprises a line sensor as described herein. Further, dispersive element 64 can also be configured to disperse the light as a function of wavelength in one direction, and as a function of the angle of incidence with respect to the sample surface in an orthogonal direction, so that simultaneous measurements as a function of both wavelength and angle of incidence are possible. In such an embodiment, detector array 66 may comprise a line sensor with resistive gate configured as described herein so as to simultaneously collect 2 or 3 spectra, each spectrum corresponding to a different range of angles of incidence. Processor 48 processes the intensity information measured by the detector array 66.

Deep ultra violet reflective spectrometry (DUV) simultaneously probes the sample with multiple wavelengths of ultra-violet light. DUV 16 uses the same spectrometer 58 to analyze probe beam 26 as BRS 14, except that DUV 16 uses the reflective lens 33 instead of focusing lens 32. To operate DUV 16, the turret containing lenses 32/33 is rotated so that reflective lens 33 is aligned in probe beam 26. The reflective lens 33 is necessary because solid objective lenses cannot sufficiently focus the UV light onto the sample.

Broadband spectroscopic ellipsometry (BSE) is discussed in pending U.S. Pat. No. 5,877,859, issued on Mar. 2, 1999 to Aspnes et al., which is incorporated by reference herein. BSE (18) includes a polarizer 70, focusing mirror 72, collimating mirror 74, rotating compensator 76, and analyzer 80. In operation, mirror 82 directs at least part of probe beam 26 to polarizer 70, which creates a known polarization state for the probe beam, preferably a linear polarization. Mirror 72 focuses the beam onto the sample surface at an oblique angle, ideally on the order of 70 degrees to the normal of the sample surface. Based upon well-known ellipsometric principles, the reflected beam will generally have a mixed linear and circular polarization state after interacting with the sample, based upon the composition and thickness of the sample's film 8 and substrate 6. The reflected beam is collimated by mirror 74, which directs the beam to the rotating compensator 76. Compensator 76 introduces a relative phase delay $\delta$ (phase retardation) between a pair of mutually orthogonal polarized optical beam components. Compensator 76 is rotated at an angular velocity $\omega$ about an axis substantially parallel to the propagation direction of the beam, preferably by an electric motor 78. Analyzer 80, preferably another linear polarizer, mixes the polarization states incident on it. By measuring the light transmitted by analyzer 80, the polarization state of the reflected probe beam can be determined. Mirror 84 directs the beam to spectrometer 58, which simultaneously measures on detector 66 the intensities of the different wavelengths of light in the reflected probe beam that pass through the compensator/analyzer combination. As explained above, detector 66 preferably comprises a line sensor with resistive gate as described herein. Processor 48 receives the output of the detector 66, and processes the intensity information measured by the detector 66 as a function of wavelength and as a function of the azimuth (rotational) angle of the compensator 76 about its axis of rotation, to solve for sample characteristics, such as the ellipsometric values $\Psi$ and $\Delta$, as described in U.S. Pat. No. 5,877,859.

Detector/camera 86 is positioned above mirror 46, and can be used to view reflected beams off of the sample 4 for alignment and focus purposes.

In order to calibrate BPE 10, BPR 12, BRS 14, DUV 16, and BSE 18, the metrology system 350 includes the wavelength stable calibration reference ellipsometer 2 that may be used in conjunction with a reference sample 4. Ellipsometer 2 includes a light source 90, polarizer 92, lenses 94 and 96, rotating compensator 98, analyzer 352 and detector 354.

Light source 90 produces a quasi-monochromatic probe beam 356 having a known stable wavelength and stable intensity. The wavelength of beam 356, which is a known constant or a measured value, is provided to processor 48 so that ellipsometer 2 can accurately calibrate the optical measurement devices in system 350.

The beam 356 interacts with polarizer 92 to create a known polarization state. In a preferred embodiment, polarizer 92 is a linear polarizer made from a quartz Rochon prism, but in general the polarization does not necessarily have to be linear, nor even complete. Polarizer 92 can also be made from calcite. The azimuth angle of polarizer 92 is oriented so that the plane of the electric vector associated with the linearly polarized beam exiting from the polarizer 92 is at a known angle with respect to the plane of incidence (defined by the propagation direction of the beam 356 and the normal to the surface of sample 4). The azimuth angle is preferably selected to be on the order of 30 degrees because the sensitivity is optimized when the reflected intensities of the P and S polarized components are approximately balanced. It should be noted that polarizer 92 can be omitted if the light source 90 emits light with the desired known polarization state.

The beam 356 is focused onto the sample 4 by lens 94 at an oblique angle. The beam 356 is ideally incident on sample 4 at an angle on the order of 70 degrees to the normal of the sample surface because sensitivity to sample properties is maximized in the vicinity of the Brewster or pseudo-Brewster angle of a material. Based upon well-known ellipsometric principles, the reflected beam will generally have a mixed linear and circular polarization state after interacting with the sample, as compared to the linear polarization state of the incoming beam. Lens 96 collimates beam 356 after its reflection off the sample 4.

The beam 356 then passes through the rotating compensator (retarder) 98, which introduces a relative phase delay $\delta_r$ (phase retardation) between a pair of mutually orthogonal polarized optical beam components. The amount of phase retardation is a function of the wavelength, the dispersion characteristics of the material used to form the compensator, and the thickness of the compensator. Compensator 98 is rotated at an angular velocity $\omega_r$ about an axis substantially parallel to the propagation direction of beam 356, preferably by an electric motor 351. Compensator 98 can be any conventional wave-plate compensator, for example those made of crystal quartz. The thickness and material of the compensator 98 are selected such that a desired phase retardation of the beam is induced. Typically a phase retardation of about 90° is convenient.

Beam 356 then interacts with analyzer 352, which serves to mix the polarization states incident on it. In this embodiment, analyzer 352 is another linear polarizer, preferably oriented at an azimuth angle of 45 degrees relative to the plane of incidence. However, any optical device that serves to appropriately mix the incoming polarization states can be used as an analyzer. The analyzer 352 is preferably a quartz Rochon or Wollaston prism.

Figure 6:
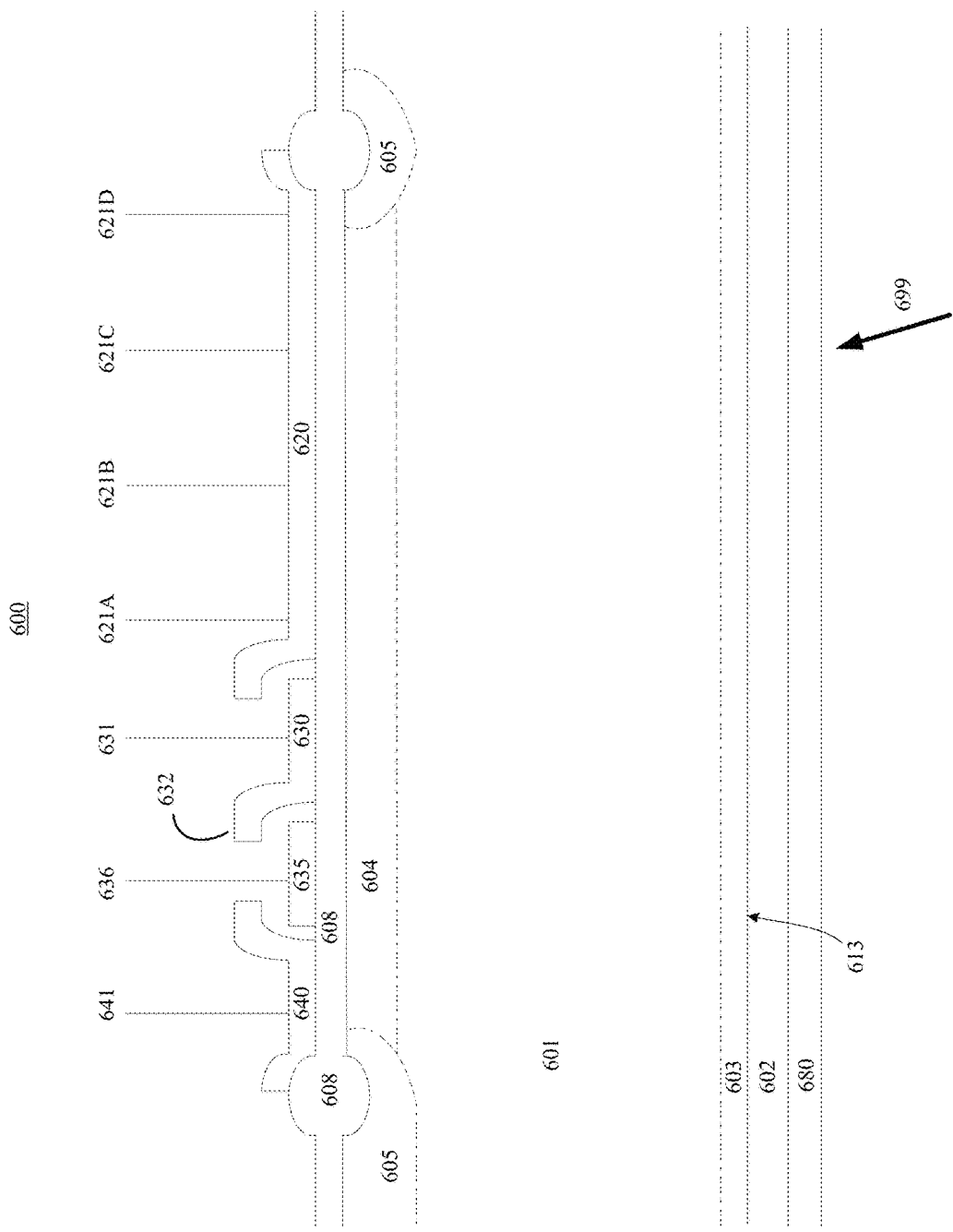
FIG. 6 is a cross-sectional view showing a pixel of an exemplary line sensor according to another specific embodiment of the present invention.

It should be noted that the compensator 98 can be located either between the sample 4 and the analyzer 352 (as shown in FIG. 6), or between the sample 4 and the polarizer 92. It should also be noted that polarizer 70, lenses 94/96, compensator 98 and analyzer 352 are all optimized in their construction for the specific wavelength of light produced by light source 90, which maximizes the accuracy of ellipsometer 2.

Beam 356 then enters detector 354, which measures the intensity of the beam passing through the compensator/analyzer combination. The processor 48 processes the intensity information measured by the detector 354 to determine the polarization state of the light after interacting with the analyzer, and therefore the ellipsometric parameters of the sample. This information processing includes measuring beam intensity as a function of the azimuth (rotational) angle of the compensator about its axis of rotation. This measurement of intensity as a function of compensator rotational angle is effectively a measurement of the intensity of beam 356 as a function of time, since the compensator angular velocity is usually known and a constant.

U.S. Pat. No. 6,297,880, which issued on Oct. 2, 2001 to Rosencwaig et al. and is incorporated by reference herein, describes metrology system 350 in further detail. U.S. Pat. No. 6,429,943, which issued on Aug. 6, 2002 to Opsal et al. and is incorporated by reference herein, describes how metrology system 350 may be used for scatterometry measurements. U.S. Pat. No. 5,608,526, which issued on Mar. 4, 1997 to Piwonka-Corle et al. and is incorporated by reference herein, describes an alternative embodiment of metrology system 350 that incorporates a spectroscopic ellipsometer and a spectrophotometer. Either, or both, of the spectroscopic ellipsometer and spectrophotometer may incorporate a line sensor with resistive gate as described herein.

Figure 4:
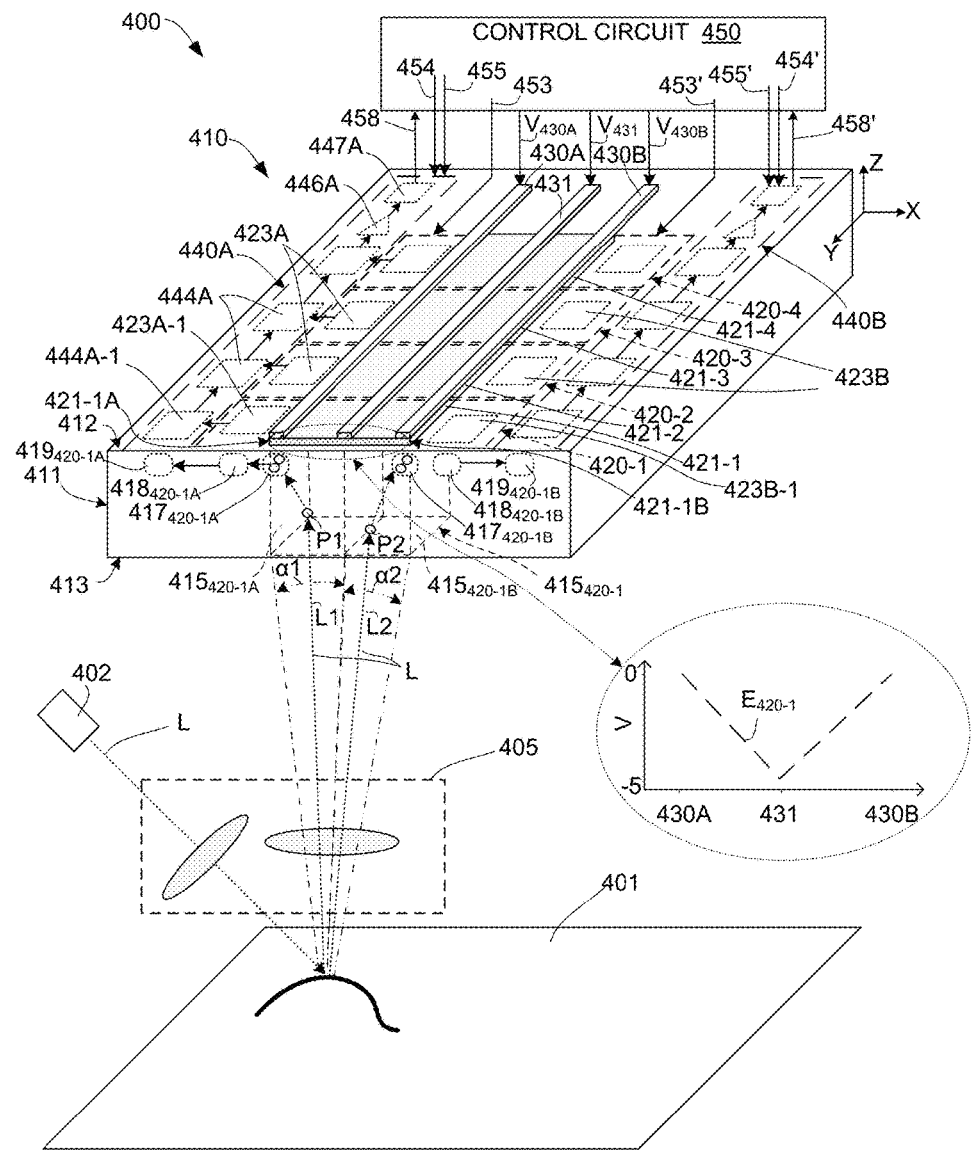
FIG. 4 illustrates an exemplary inspection system including a simplified line sensor according to an embodiment of the present invention.

FIG. 4 illustrates a simplified system 400 for inspecting or measuring a sample 401 in accordance with an exemplary embodiment of the current invention. System 400 generally includes an illumination source 402 configured to generate radiation (e.g., light) L, an optical system (optics) 405 configured to direct radiation L from illumination source 402 to sample 401, and to direct radiation output or reflected from sample 401 to a sensor 410. System 400 also includes a control circuit 450, which may be integrated onto (i.e. part of) sensor 410 or fabricated separate from sensor 410.

Line sensor 410 is fabricated on an upper surface 412 of a semiconductor substrate 411 (e.g., p-doped epitaxial silicon), and generally includes four light-sensitive pixels 420-1 to 420-4 formed over upper surface 412, at least three elongated aperture control electrodes 430A, 430B and 431, and one or more readout circuits 440A and 440B. Those skilled in the art will recognize that the depicted sensor is greatly simplified in order to describe novel features associated with the present invention, and that practical line sensors include additional circuit structures and utilize a substantially larger number of pixels.

As indicated in FIG. 4, pixels 420-1 to 420-4 are rectangular or square in shape, and are arranged in a row. Pixels 420-1 to 420-4 respectively include resistive polysilicon control gates 421-1 to 421-4 and buffer/transfer gates 423A and 423B. Resistive control gates 421-1 to 421-4 are generally elongated lightly doped polysilicon structures that are attached to upper surface 412 by way of an intervening dielectric layer (not shown), and extend in a lengthwise direction (i.e., measured in the X-axis direction) between opposing end portions. For example, resistive control gate 421-1 of pixel 420-1 extends between a first end portion 421-1A and a second end portion 421-1B in the lengthwise (X-axis) direction. Resistive control gates 421-1 to 421-4 are typically joined together in a widthwise direction (i.e., the control gates are formed by portions of a contiguous polysilicon layer extending in the Y-axis direction indicated in FIG. 4), though, in an alternative embodiment, they are separated by gaps. Each resistive control gate 421-1 to 421-4 defines its pixel's associated total (maximum) light sensitive region, which is generally formed by portions of substrate 411 disposed below each resistive control gate. For example, as indicated in FIG. 4, associated light sensitive region $415_{420-1}$ of pixel 420-1 is formed by a corresponding portion of substrate 411 located below resistive control gate 421-1. Buffer/transfer gates 423A and 423B are disposed adjacent to the end portions of resistive control gates 421-1 to 421-4, and are fabricated on substrate 411 using known techniques and configured facilitate the storage and transfer of charges collected by pixels 420-1 to 420-4 during operation of sensor 410. For example, buffer/transfer gate 423-1A of pixel 420-1 is configured to generate a charge accumulation region $417_{420-1A}$ below end portion 421-1A of control gate 421-1 for collecting charges during an integration period of sensor operation, and configured to facilitate transfer the collected charges from charge accumulation region $417_{420-1A}$ to a readout region $419_{420-1A}$ (e.g., by way of transfer region $418_{420-1A}$) during a readout period of sensor operation.

According to an aspect of the present invention, control circuit 450 is configured to apply aperture control signals by way of aperture control electrodes 430A, 430B and 431 to resistive control gates 421-1 to 421-4 such that resistive control gates 421-1 to 421-4 generate electric fields in the light sensitive regions of pixels 420-1 to 420-4. Aperture control electrodes 430A, 430B and 431 are elongated (e.g., metal) structures that extend in parallel across pixels 420-1 to 420-4, and are electrically connected to corresponding regions of resistive control gates 421-1 to 421-4. For example, a first end electrode 430A contacts first end portion 421-1A of resistive control gate 421-1, a second end electrode 430B contacts second end portion 421-1B of each said resistive control gate e.g., 421-1, and a central electrode 431 is disposed between first end electrode 430A and second end electrode 430B and contacts a central region of control gate 421-1. During sensor operation, control circuit 450 applies a first aperture control signal $V_{430A}$ onto first end electrode 430A, a second aperture control signal $V_{430B}$ onto second end electrode 430B, and a third aperture control signal $V_{431}$ onto central electrode 431. During operating periods when non-monotonic voltage profiles are desired, control circuit 450 simultaneously generates and applies aperture control signals $V_{430A}$, $V_{430B}$ and $V_{431}$ onto aperture control electrodes 430A, 430B and 431 such that aperture control signals $V_{430A}$ and $V_{430B}$ are more positive (i.e., have a more positive voltage level) than aperture control signal $V_{431}$. For example, aperture control signals $V_{430A}$ and $V_{430B}$ are generated with 0V voltage levels, and aperture control signal $V_{431}$ is generated with a −5V voltage level. By applying more positive voltage levels to the end portions of each resistive control gate and a more negative voltage level to a central region of each resistive control gate, each resistive control gate is caused to generate an electric field such that photoelectrons generated in an associated light sensitive region are driven by the electric field into one of two or more different charge accumulation regions. For example, as indicated in FIG. 4, aperture control signals $V_{430A}$, $V_{431}$ and $V_{430B}$ create a non-monotonic voltage profile $E_{420-1}$ (depicted by a "V" shaped potential diagram) in resistive control gate 421-1 that generates an electric field that effectively separates associated light sensitive region $415_{420-1}$ into two portions $415_{420-1A}$ and $415_{420-1B}$ that are generally disposed opposite sides of the negative peak value of non-monotonic voltage profile $E_{420-1}$. When sensor 410 is operated with a non-monotonic voltage profile $E_{420-1}$, photoelectrons (e.g., photoelectron P1) generated in light sensitive portion $415_{420-1A}$ are driven by the electric field created by that non-monotonic voltage profile $E_{420-1}$ into charge collection regions $417_{420-1A}$, and photoelectrons (e.g., photoelectron P2) generated in light sensitive portion $415_{420-1B}$ are driven by the electric field into charge collection regions $417_{420-1B}$. The aperture size of pixels 420-1 to 420-4 is thereby effectively reduced to that of light sensitive portion $415_{420\text{-}1A}$ by way of subsequently reading out and measuring only the charges collected in one set of charge collection regions (e.g., from charge collection region $417_{420\text{-}1A}$) and ignoring (e.g., discarding) the charges collected in the other set of charge collection regions (e.g., in charge collection region $417_{420\text{-}1B}$). Accordingly, the present invention facilitates electrically controlling the aperture size of pixels 420-1 to 420-4 by way of elongated electrical connections (electrodes) 430A, 430B and 431, which contact different locations on each resistive gate in order to facilitate the generation of potential gradients (electric fields). More than two such electrical connections are required in order to generate non-monotonic voltage profiles in the resistive gate.

Immediately adjacent to pixels 420-1 to 420-4 is at least one readout circuit 440A including charge-coupled device (CCD) readout registers 444A. Each readout register 444A is connected to a charge conversion amplifier 446A and buffer 447A that generates an output signal 458. Readout registers 444A are controlled by multiple clock signals 454 and 455, which are generated by control circuit 450 along with other control signals (not shown) such as buffer gate and transfer gate control signals. Although a two phase clock generated by clock signals 454 and 455 is shown, readout registers using three and four phase clocks are known in the art and could be used.

Referring again to FIG. 4, during operation light L generated by illumination source 402 is directed by way of optical system (optics) 405 onto sample 401, and redirected light output or reflected from sample 401 is directed to sensor 410, also by way of optics 405, and enters sensor 410 through lower (bottom) surface 413. According to an aspect of the present embodiment, optics 405 are configured to direct radiation (light) L from sample 401 to sensor 410 in the form of a confocal image. In one specific embodiment, optics 405 are configured to direct radiation disposed within corresponding angle ranges from sample 401 to sensor 410 such that light transmitted from similar structural locations or angles is directed into similar portions of each pixel's light sensitive region. For example, optics 405 are configured such that first light portions L1 directed within a first range of angles α1 from sample 401 to sensor 410 are directed into a first light sensitive portion $415_{420\text{-}1A}$ of associated light sensitive region $415_{420\text{-}1}$ of pixel 420-1, and such that second light portions L2 directed within a second range of angles α2 from sample 401 to sensor 410 are directed into a second light sensitive portion $415_{420\text{-}1B}$ of light sensitive region $415_{420\text{-}1}$. Note that first light sensitive portion $415_{420\text{-}1A}$ is closer to first end portion 421-1A of resistive control gate 421-1 than second light sensitive portion $415_{420\text{-}1B}$, and second light sensitive portion $415_{420\text{-}1B}$ is located closer to second end portion 421-1B than first light sensitive portion $415_{420\text{-}1A}$. The radiation (light) L entering each light sensitive portion is absorbed and generates photoelectrons that are collected during an integration period, and then sequentially measured during a subsequent readout period. For example, FIG. 4 depicts a first photoelectron P1 generated in first light sensitive portion $415_{420\text{-}1A}$ of light sensitive region $415_{420\text{-}1}$ in response to light portion L1, and depicts a second photoelectron P2 generated in second light sensitive portion $415_{420\text{-}1B}$ in response to light portion L2. The voltage profile generated on resistive control gates 421-1 to 421-4 controls which photoelectrons accumulate at which location within each pixel 420-1 to 420-4. For example, when resistive control gate 421-1 is driven by way of aperture control signals $V_{430A}$ and $V_{430B}$ having 0V values and aperture control signal $V_{431}$ having a negative 5V (−5V) value, resistive control gate 421-1 generates a non-monotonic voltage profile $E_{420\text{-}1}$ in associated light sensitive region $415_{420\text{-}1}$ that drives first photoelectron P1, which is generated by first light portion L1 in first light sensitive portion $415_{420\text{-}1A}$, into first charge accumulation region $417_{420\text{-}1A}$, and simultaneously drives second photoelectron P2 generated by second light portions L2 in a second light sensitive portion $415_{420\text{-}1B}$ into second charge accumulation region $417_{420\text{-}1B}$. At the end of the integration period, buffer/transfer gates 423A-1 controls the transfer of the accumulated photoelectron charge from charge accumulation region $417_{420\text{-}1A}$ into a transfer region $418_{420\text{-}1A}$, and then into a corresponding region $419_{420\text{-}1A}$ of readout register 444A-1. Clock signals 454 and 455, which are generated by control circuit 450, are utilized to then control the transfer of charges sequentially from one register 444A to the next and from the last register to charge conversion amplifier 446A and buffer 447A. Hence, the charge captured by each pixel 420-1 to 420-4 in the manner described above in turn is output as a voltage or current output signal 458 to control circuit 450.

In alternative embodiments, charges generated by photoelectrons entering the second light sensitive portions (e.g., light sensitive portion $415_{420\text{-}1B}$ in FIG. 4) are either discarded (i.e., coupled to ground or otherwise erased) or read out simultaneously with the charges generated by photoelectrons entering the selected light sensitive portion (e.g., light sensitive portion $415_{420\text{-}1A}$ in FIG. 4). To facilitate readout of the charges from the second light sensitive portions, sensor 410 includes an optional second readout circuit 440B that is disposed on the second end of pixels 420-1 to 420-4 including registers, amplifiers and buffers that are coupled to transfer gates 423B and function in the manner described above with reference to readout circuit 440A.

Although FIG. 4 illustrates how aperture control electrodes 430A, 430B and 431 may be used to select different angles of radiation from sample 401, in an alternative embodiment, optics 405 are configured so that control electrodes 430A, 430B and 431 can be used to select radiation from different locations of sample 401.

FIGS. 5A to 5D are a simplified diagrams illustrating how different non-monotonic voltage profiles may be created by way of generating different voltage profiles in resistive control gates using more than three aperture control electrodes.

Figure 5A:
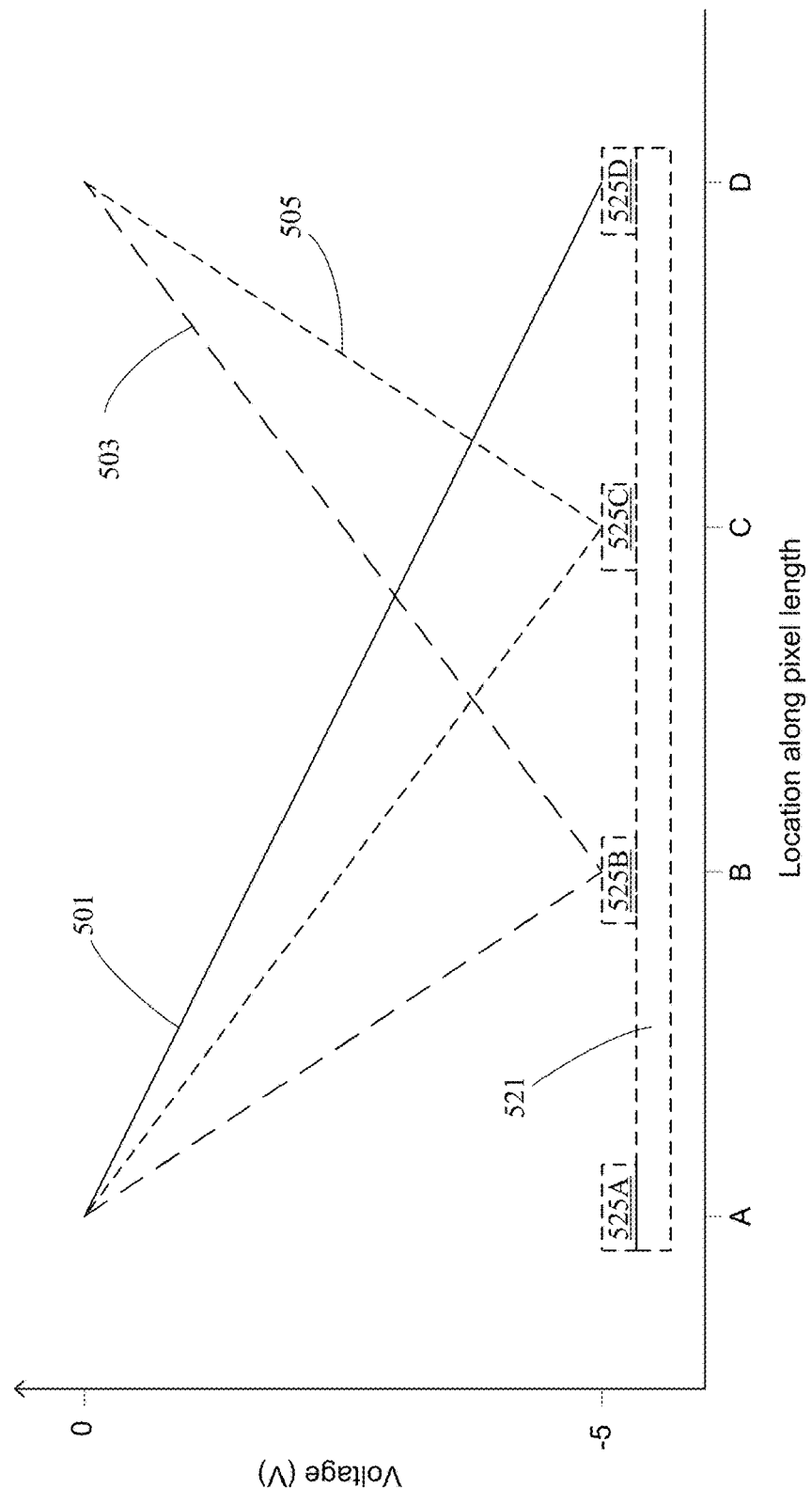
FIGS. 5A, 5B, 5C and 5D illustrate exemplary voltage profiles that can be applied to resistive control gates according to alternative embodiments of the present invention.

FIG. 5A depicts different voltage schemes that may be applied to a resistive control gate 521 (shown in dashed lines for reference) by way of four aperture control electrodes (i.e., end electrodes 525A and 525D at locations A and D along the length of resistive control gate 521, and two central electrodes 525B and 525C at locations B and C, along the length of resistive control gate 521). In a manner similar to that described above with reference to FIG. 4, different voltages may be applied to electrodes 525A to 525D to create potential differences between different locations within resistive control gate 521, thereby adjusting the effective pixel aperture size by way of causing resistive control gate 521 to generate different electric fields. Examples of different potentials that may be applied to resistive control gate 521 are indicated by lines 501, 503 and 505 in FIG. 5A. In one embodiment, during the process of inspecting (e.g., detecting and/or measuring features of) a sample, the electric fields generated by resistive control gate 521 are changed during respective time periods by way of changing the aperture control signals (voltages) applied to electrodes 525A to 525D (e.g., between those depicted by lines 501, 503 and 505).

The voltage profile indicated by line 501 in FIG. 5A depicts an approximately linear voltage gradient between −5V at location D (which corresponds to the location of end electrode 525D) and 0V at location A (which corresponds to the location of end electrode 525A). Locations B and C (which correspond to the locations of central electrodes 525B and 525C) are at voltages intermediate in values between 0 and −5V. Because the voltages applied at locations A and D produce an approximately linear voltage gradient along resistive control gate 521, central electrodes 525B and 525C at locations B and C may not need to be driven when approximately linear voltage gradient 501 is desired. The voltage on resistive control gate 521 induces charges in the substrate near the surface of the light sensitive region just underneath control gate 521, and hence creates a potential gradient (electric field) in the substrate. Since electrons are negatively charged, each photoelectron will rapidly migrate towards the most positive potential in its vicinity. Hence, with an approximately linear gradient like that depicted by line 501 of FIG. 5A, the photoelectrons will only accumulate near location A. Because location A corresponds to the location of contact 525A, this approximately linear potential gradient causes substantially all photoelectrons generated in the light sensitive region of the corresponding pixel to accumulate in a charge accumulation region underneath electrode 525A, whereby the accumulated charge may be subsequently transferred to a readout register in the manner described above with reference to FIG. 4.

Line 503 in FIG. 5A illustrates a second voltage profile generated on resistive control gate 521 in accordance with an exemplary embodiment of the present invention. Location B is held at −5V by way of an associated aperture control signal applied to central electrode 525B while locations A and D are held at 0V by way of end electrodes 525A and 525D. Location C may be driven to an intermediate voltage between −5V and 0V such as about −2.5V by way of electrode 525C, or it may be left floating. In this state, the effective pixel aperture size is defined between locations A and B. That is, photoelectrons created in the substrate underneath resistive control gate 521 between locations A and B will quickly migrate underneath location A because it is the most positive potential in that region. Photoelectrons created in the substrate underneath resistive control gate 521 between locations B and D will quickly migrate to a charge accumulation region located adjacent location D (e.g., underneath electrode 525D) as it is the most positive potential in that region of the pixel. The accumulated charge near location A can be read out of the pixel into a readout register, such as register 444A-1 shown in FIG. 4. The accumulated charge near location D may be discarded by collecting it, for example, with an overflow drain or scupper drain located near location D, or alternatively the charge may be read out of the pixel into a second readout circuit, such as circuit 440B as shown in FIG. 4. Because this voltage gradient causes the sensor to collect the signal corresponding to light that hits the sensor between locations A and B, while separating or discarding the signal corresponding to light that hits the sensor between locations B and D, the voltage gradient acts like an aperture or beam divider that, in effect, blocks or separates light that arrives at the sensor between locations B and D, while transmitting light that arrives at the sensor between locations A and B to an output signal, such as output signal 458 in FIG. 4. Unlike a mechanical aperture, no extra physical space is required in front of the sensor to accommodate that aperture. Furthermore, since the voltage gradients are controlled electrically, they can be changed very quickly, for example, in a few microseconds or less, which is much faster than a mechanical aperture can be changed.

Line 505 in FIG. 5A illustrates yet another example voltage profile on resistive control gate 521, and shows how pixel aperture size may be adjusted by way of changing the voltages applied to resistive control gate 521. In this case, location C is held at −5V by way of an associated aperture control signal applied to electrode 525C while locations A and D are held at 0V by way of end electrodes 525A and 525D (location B is floating or held at an intermediate voltage). In this state, the effective pixel aperture size is between locations A and C. That is, photoelectrons created in the substrate underneath resistive control gate 521 between electrodes 525A and 525C will quickly migrate to the charge accumulation region underneath electrode 525A because it is the most positive potential in that region. Photoelectrons created in the substrate underneath resistive control gate 521 between electrodes 525C and 525D will quickly migrate to the charge accumulation region underneath electrode 525D as it is the most positive potential in that region of the pixel. The accumulated charge near location A can be read out of the pixel into a readout register, such as register 444A-1 shown in FIG. 4, and the accumulated charge near location D may be discarded or read out into a readout circuit, such as circuit 440A shown in FIG. 4.

Although the example of FIG. 5A utilizes four locations A, B, C and D for controlling the voltage gradient applied to resistive control gate 521 by way of four contact (electrodes) 525A, 525B, 525C and 525D, three contacts could be used (as in the exemplary embodiment of FIG. 4), or more than four contacts can be used (as illustrated in the following embodiments). Three contacts allow the full pixel to be selected and directed to an output, or allow the pixel to be divided into two parts (one "aperture"). Four contacts allow the selection of two different "aperture" sizes or two different divisions of the pixel in addition to the full pixel. More than four contacts would allow more than two different "aperture" sizes.

Figure 5B:
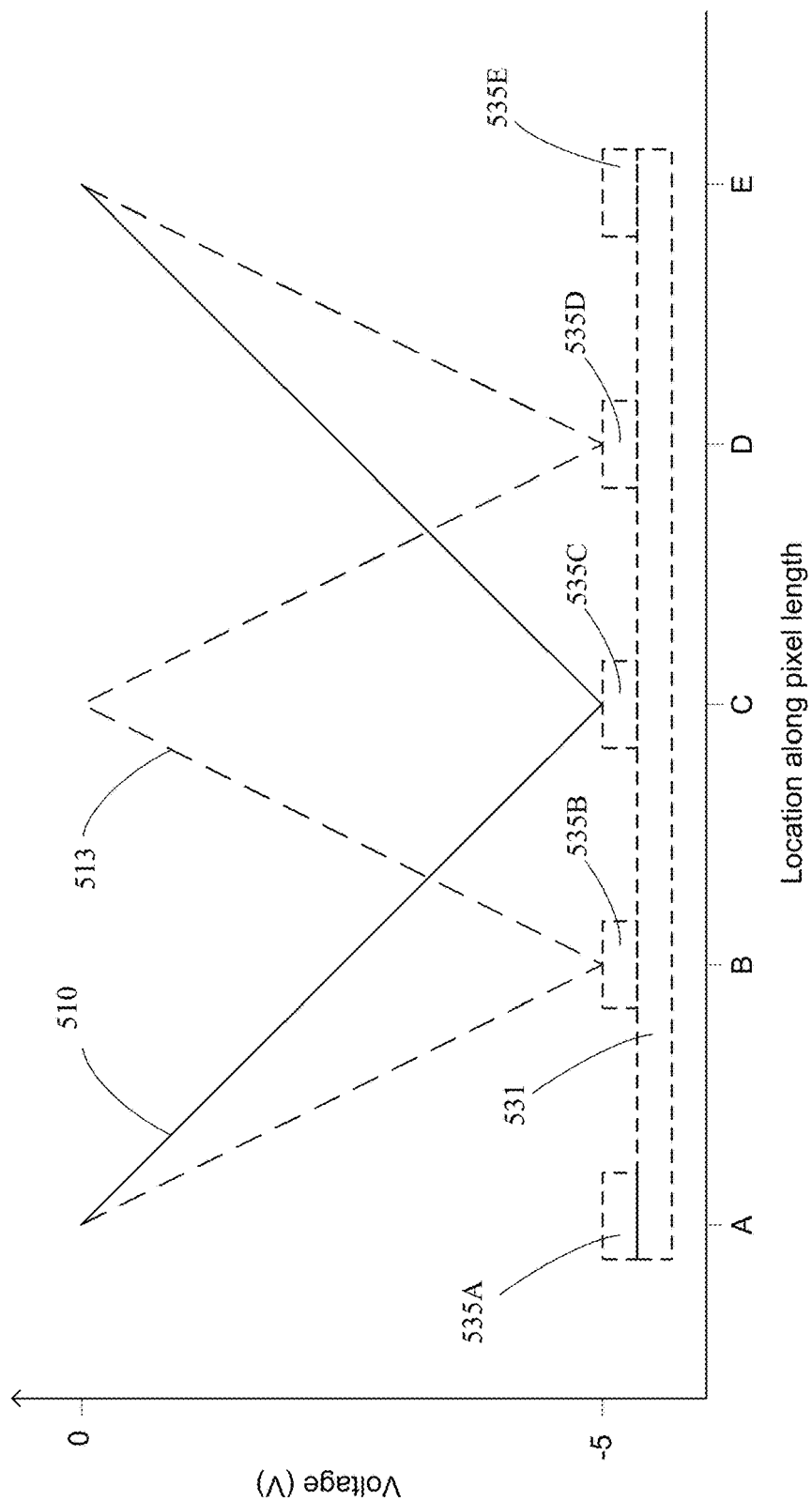

FIG. 5B depicts different voltage schemes that may be applied to a resistive control gate 531 by way of five aperture control electrodes (i.e., end electrodes 535A and 535E and three central electrodes 535B, 535C and 535D, all shown in dashed lines for reference) respectively disposed at five different locations (A, B, C, D and E) along the length of resistive control gate 531. In a manner similar to that described above with reference to FIGS. 4 and 5A, different voltages are applied by a control circuit (not shown) to electrodes 535A to 535E to create potential differences between different locations within resistive control gate 531, thereby adjusting the effective pixel aperture size by way of causing resistive control gate 531 to generate associated electric fields. Lines 510 and 513 in FIG. 5B depict two exemplary non-monotonic voltage profiles applied to resistive control gate 531, which forms part of a corresponding pixel of a line sensor similar to line sensor 410 of FIG. 4.

Line 510 in FIG. 5B depicts a voltage profile generated during a first time period and comprising two approximately linear voltage gradients between −5V at location C (central electrode 535C) and 0V at locations A and E (end electrodes 535A and 535E). During this time period, central electrodes 535B and 535D at locations B and D are floating or otherwise maintained at voltages intermediate in values between 0 and −5V. Photoelectrons created in the substrate underneath resistive control gate 531 between locations A and C will quickly migrate to the charge accumulation region near location A (underneath end electrode 535A)

because it is the most positive potential in that region. Photoelectrons created in the substrate underneath resistive control gate 531 between locations C and E will quickly migrate underneath location E as it is the most positive potential in that region of the pixel. At the end of the time period, accumulated charge near location A can be read out of the pixel into a readout register, such as register 444A-1 shown in FIG. 4. The accumulated charge near location E may be discarded by collecting it, for example, with an overflow drain or scupper drain located near location E, or alternatively the charge may be read out of the pixel into a second readout circuit, such as circuit 440B as shown in FIG. 4.

Line 513 in FIG. 5B depicts a second voltage profile generated during a second time period (e.g., subsequent to or before the first time period) and comprising four approximately linear voltage gradients by applying a more negative voltage (e.g., −5V) to electrodes 535B and 535D at locations B and D, and by simultaneously applying a more positive voltage (e.g., 0V) to electrodes 535A, 535C and 535E at locations A, C and E. Photoelectrons created in the substrate underneath resistive gate 531 between locations A and B will quickly migrate underneath location A because it is the most positive potential in that region. Photoelectrons created in the substrate underneath resistive control gate 531 between locations D and E will quickly migrate underneath location E as it is the most positive potential in that region of the pixel. Photoelectrons created in the substrate underneath resistive gate 531 between locations B and D will quickly migrate underneath location C because it is the most positive potential in that region. The accumulated charge near location A can be read out of the pixel into a readout register, such as register 444A-1 shown in FIG. 4. The accumulated charge near location E may be read out of the pixel into a second readout circuit, such as circuit 440B as shown in FIG. 4. The accumulated charge near location C can be subsequently read out of the pixel, for example, by first changing the voltage profile on resistive control gate 531 (e.g., to a profile such as 501 shown in FIG. 5A or 510 shown in FIG. 5B) such that the charge accumulated at location C is driven to one or both end locations A and/or E. Once the charge has been moved to one or both sides of the pixel, it can be transferred to readout circuits such as circuits 440A or 440B shown in FIG. 4. In such a way the sensor may be configured to simultaneously collect three image data values, even though the sensor has only two readout circuits (i.e., circuits 440A or 440B shown in FIG. 4).

Figure 5C:
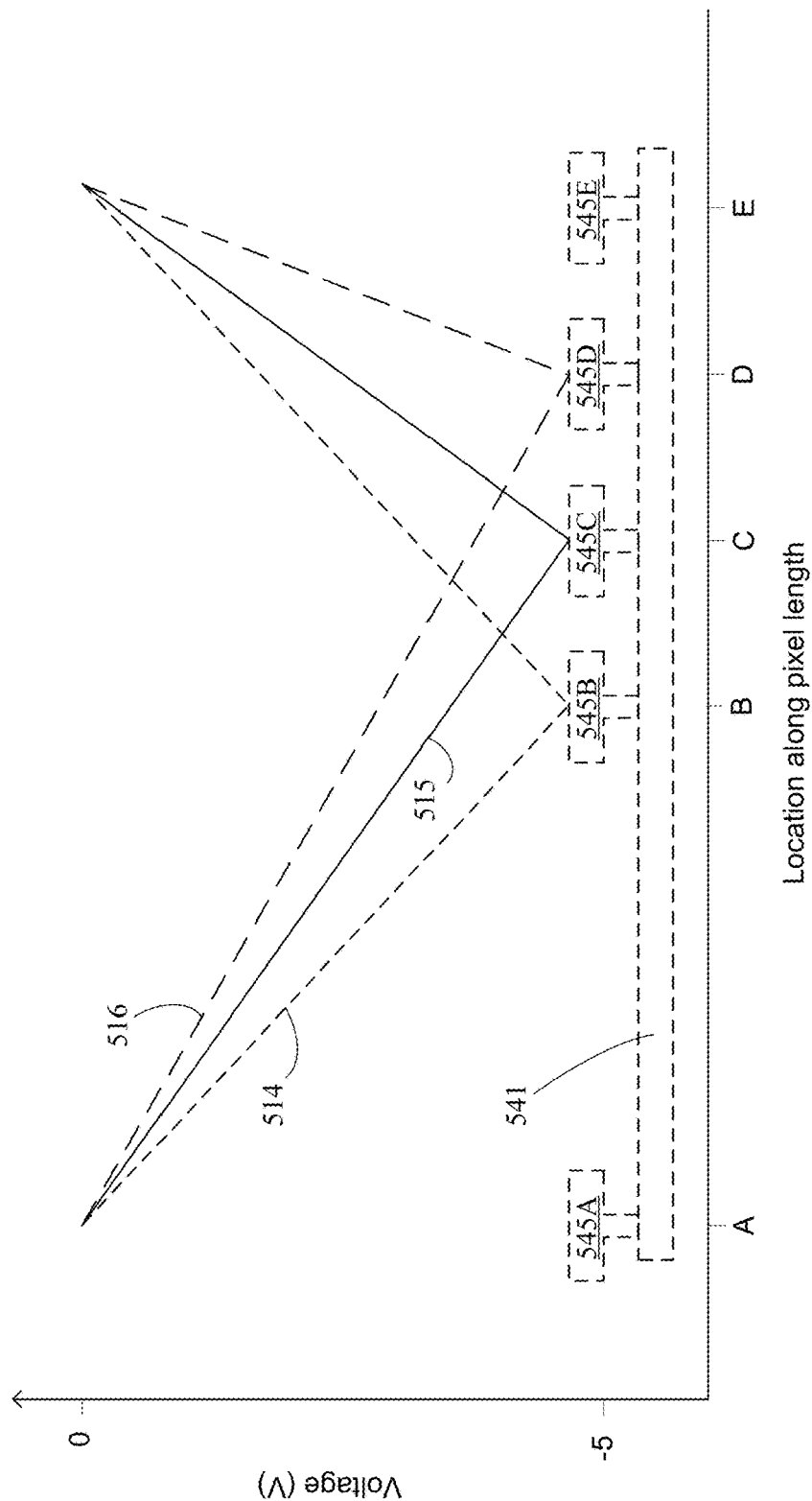

FIG. 5C depicts different voltage schemes that may be applied to a resistive control gate 541, which forms part of a corresponding pixel of a line sensor similar to line sensor 410 of FIG. 4, by way of five aperture control electrodes (i.e., end electrodes 545A and 545E and three central electrodes 545B, 545C and 545D) respectively disposed at five different locations (A, B, C, D and E) along the length of resistive control gate 541. In this example, central electrodes 545B, 545C and 545D are offset in the direction of location E to facilitate incremental fine adjustments to the effective aperture size of each pixel. Specifically, in a manner similar to that described above with reference to FIGS. 4 and 5A, different voltages are applied by a control circuit (not shown) to electrodes 545A to 545E to create potential differences between different locations within resistive control gate 541, thereby adjusting the effective pixel aperture size of each pixel by way of causing resistive control gate 541 to generate associated electric fields. Lines 514, 515 and 516 in FIG. 5C depict three exemplary non-monotonic voltage profiles generated by way of applying relatively positive voltages (e.g., 0V) to end electrodes 545A and 545E and corresponding alternative relatively negative voltages (e.g., −5V) to central electrodes 545B, 545C and 545D, thereby generating a relatively small aperture size (i.e., between locations A and B), a medium aperture size (i.e., between locations A and C), and a relatively large aperture size (i.e., between locations A and D), respectively. As explained in the previous examples, charges accumulated at location A are subsequently read out at the end of each time period. The approach depicted in FIG. 5C can be used to finely adjust the effective aperture size of all pixels of a sensor in order to optimize the light collection, or may be used to adjust the effective aperture size of each individual pixel during a calibration period to such that all pixels of the sensor have a uniform aperture size.

Figure 5D:
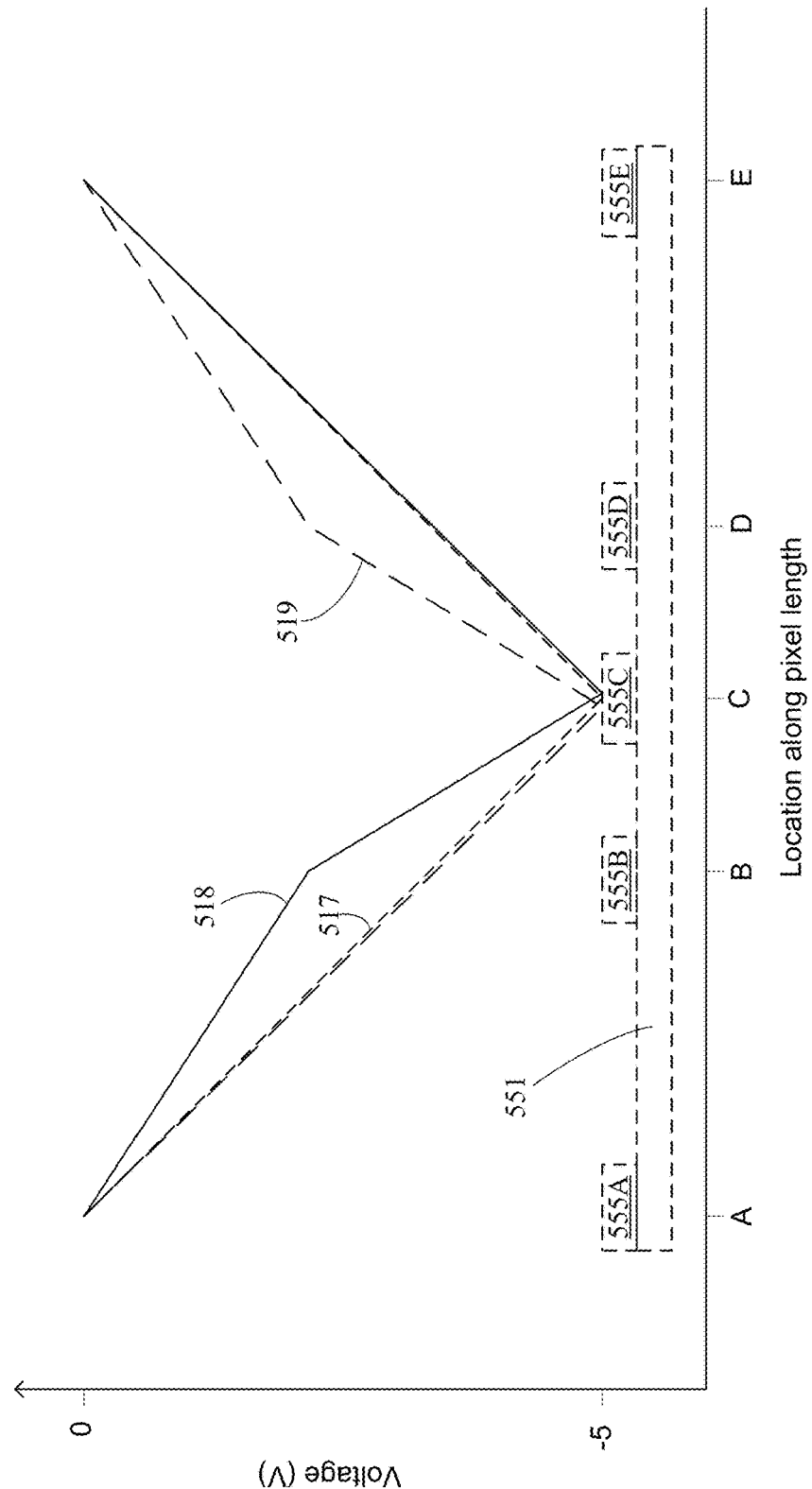

FIG. 5D depicts different voltage schemes that may be applied to a resistive control gate 551, which forms part of a corresponding pixel of a line sensor similar to line sensor 410 of FIG. 4, by way of five aperture control electrodes (i.e., end electrodes 555A and 555E and three central electrodes 555B, 555C and 555D) respectively disposed at five different locations (A, B, C, D and E) along the length of resistive control gate 551. In this example, central electrodes 555B and 555D are disposed closer to central electrode 555C (central location C) to facilitate further incremental fine adjustments to the effective aperture of each pixel by way of generating fringing fields. Specifically, in a manner similar to that described above with reference to FIGS. 4 and 5A, a symmetric "V" shaped non-monotonic voltage profile, which is depicted by line 517, is generated by applying a negative voltage (e.g., −5V) to central electrode 555C and more positive voltages (e.g., 0V) to end electrodes 555A and 555E (central electrodes 555B and 555D are floating). To shift the effective pixel aperture edge to the right (i.e., toward location E), an intermediate adjustment voltage (e.g., −2.5V) is applied to central electrode 555B, thereby producing a voltage profile depicted by line 518 that causes resistive gate electrode 541 to generate a corresponding asymmetric electric field shifted toward location E. Conversely, to shift the effective pixel aperture edge to the left (i.e., toward location A), an intermediate adjustment voltage (e.g., −2.5V) is applied to central electrode 555D, thereby producing a voltage profile depicted by line 519 that causes resistive gate electrode 541 to generate a corresponding asymmetric electric field shifted toward location A. The approach depicted in FIG. 5D can be used to continuously adjust the pixel edge location during operation by way of changing the adjustment voltages applied to central electrodes 555B and 555D.

Although the examples of FIGS. 5A to 5D shows voltages gradients between −5V and 0V, this is merely an example of voltage ranges that can be useful. For example, voltage gradients between about −6V and −1V or about −4V and +1V would have a substantially similar effect as gradients between −5V and 0V and could be used instead. Though a voltage difference of about 5V is a convenient value for a pixel that is about 100 μm long, a smaller voltage difference could be used, particularly if the pixel were shorter than about 100 μm. The voltage difference could be larger than 5V. A larger voltage difference could be particularly useful if the pixel is longer than about 150 μm. Note also that voltage values are necessarily relative to an arbitrary choice of a zero volt reference. Although ground is most usually chosen as the zero-volt reference, in some applications, such as detection of electrons or other charged particles, the whole sensor may be floated at a potential away from ground. For the exemplary voltages used herein, unless otherwise stated, it can be assumed that the surface of the sensor on which light (or charged particles) is incident is within a few volts of zero volts.

FIG. 6 illustrates an exemplary line sensor 600 in cross-section according to another specific embodiment of the present invention. Sensor 600 is fabricated in a semiconductor membrane 601 (e.g., a layer of lightly p-doped epitaxial silicon) that was grown on a silicon wafer (not shown) and then exposed by polishing or etching from the backside. The dopant concentration in epitaxial silicon 601 is preferably about $2 \times 10^{13}$ atoms $cm^{-3}$ or less.

Light 699 is incident on sensor 600 from below. In one embodiment, a pure boron layer 602 of a few nm thickness (such as a thickness between about 2 nm and about 6 nm) is deposited on the bottom (illuminated) surface of epitaxial silicon 601 to prevent oxidation and make sensor 600 resilient against damage from exposure to DUV radiation and charged particles. Since DUV light is particularly useful for inspection and measurements of small features on semiconductor wafers, sensors with multi-year lifetimes under continuous exposure to DUV radiation are particularly useful in semiconductor inspection and metrology systems. In an alternate embodiment, pure boron layer 602 is omitted. Such an embodiment may be useful where the average DUV power density incident on sensor 600 is low enough that sensor degradation is minimal, such as a DUV power density less about 20 µW $cm^2$ (in general shorter wavelength light is more damaging, so systems using very short wavelengths and lower power densities might benefit from the pure boron layer 602, whereas another system using longer wavelengths and a higher power density might have acceptable sensor lifetime without the boron layer 602).

During the deposition of the pure boron layer 602 on the bottom surface, some boron diffuses into the silicon forming a highly p-doped layer of silicon 603 just a few nm thick adjacent to the pure boron layer 602. In one embodiment, this is achieved by holding the wafer containing sensor 600 at an elevated temperature, such as a temperature between about 800° C. and about 900° C. for a few minutes immediately following deposition of the pure boron layer 602. The highly p-doped silicon layer 603 creates a built-in electric field that drives any photoelectrons created near the back surface of the silicon away from that bottom surface. This built-in field is very important because most DUV radiation is absorbed within 10 to 15 nm of the silicon surface. If any of those photoelectrons reach the surface, there is a high probability that they will recombine and be lost thus reducing the quantum efficiency (QE) of sensor 600. A strong built-in field is required to very quickly drive the photoelectrons away from the silicon surface in order to have high QE at DUV wavelengths. In a sensor where pure boron layer 602 is not present, ion implantation or other doping technique must be used to create highly p-doped silicon layer 603.

In a preferred embodiment an anti-reflection coating 680 is formed over lower surface 613 (e.g., deposited onto boron coating 602, or directly onto lower surface 613 of epitaxial silicon 601 in embodiments where pure boron coating 602 is not present). Because both boron and silicon have high absorption coefficients for DUV light, they reflect light strongly. The QE of sensor 600 can be significantly improved by using an anti-reflection layer 680. Anti-reflection coating 680 may comprise one or more layers of dielectric materials such as silicon dioxide, aluminum oxide and magnesium fluoride. If the sensor is not required to operate at DUV wavelengths, a wider range of materials may be used for the anti-reflection coating 680 including, in addition to those just listed, hafnium dioxide and silicon nitride.

Charged particle sensors typically do not require an anti-reflection coating. In such sensors, layer 680 may be omitted, or may comprise a thin conductive coating, such as a few-nm thick layer of a refractory metal.

A dielectric layer 608 is deposited or grown on the top surface of the epitaxial silicon 601. Dielectric layer 608 may comprise a silicon dioxide layer, or it may comprise two or three layers such as silicon nitride on silicon dioxide or silicon dioxide on silicon nitride on silicon dioxide. Typically the thickness of dielectric layer 608 is in the range of about 50 nm to about 200 nm. A layer of n-type silicon 604 is created under the front surface as a buried channel to collect photoelectrons.

Multiple gate electrodes such as 630, 635 and 640 are deposited and patterned on top of dielectric layer 608. The gate electrodes are typically made of polysilicon or aluminum, but other conductive materials including other metals and semi-metallic compounds (such as TiN) may be used. Electrical connections such as 631, 636 and 641 may be made to the gate electrodes. Although FIG. 6 depicts gates electrodes such as 630, 635 and 640 only on the left side of resistive gate 620, similar structures may also be present on the right side of resistive gate 620 in order to allow readout from both sides of the pixel as illustrated by readout circuits 440A and 440B in FIG. 4.

In preferred embodiments, the gate electrodes overlap one another, as shown, for example, at 632 in order to minimize and control fringe electric fields near the edges of the electrodes. The gate electrodes are separated by a dielectric material (not shown).

Resistive gate 620, preferably comprising undoped or lightly doped poly-crystalline silicon (poly-silicon), overlays the light-sensitive pixel. Multiple electrical connections are made to different locations on the resistive gate. These connections (or contacts) are shown schematically by 621A, 621B, 621C and 621D. Although four electrical connections are shown, three, four or more may be used depending on how many different light collecting modes are needed. As explained above, voltage gradients are created in resistive gate 620 by applying different voltages to the different contacts 621A, 621B, 621C, 621D connected to it. Different locations along the length of the resistive gate are at different voltages as a result of the different voltages applied to the contacts as illustrated in FIGS. 5A and 5B. The potential at the surface of the epitaxial silicon 601 varies with location according to the voltage at the corresponding location on resistive gate 620. This varying potential creates an electric field in the epitaxial layer 601 that controls where the photoelectrons collect. Because the epitaxial layer 601 is lightly doped, there are few free carriers and the electric fields from charges near the surface will extend throughout all, or almost all, of the epitaxial layer 601.

For example, if contact 621A is more positive than contact 621D and contacts 621B and 621C are at intermediate voltages such that an approximately linear voltage gradient exists on resistive gate 620 between the location of contact 621D and contact 621A, then the electric field within the epitaxial silicon 601 will drive photoelectrons to a location beneath contact 621A.

If buffer gate 630 is held at a more negative voltage than 621A, electrons will not move underneath buffer gate 630. In order to readout the accumulated charge the voltage on buffer gate 630 can be raised by, for example, applying a voltage to contact 631 that is more positive than the voltage applied to contact 621A. Raising the potential on transfer gate 635 by applying an appropriate voltage to contact 636 can move electrons from under buffer gate 630 to under transfer gate 635. The potential on buffer gate 630 may be lowered at the same time as, or slightly later than, the potential on transfer gate 635 is raised to block direct transfer of electrons from the pixel under transfer gate 635. Optional additional transfer gates, buffer gates or readout registers, such as 640, may be included as needed. Ultimately the electrons are transferred to a floating diffusion region (not shown), which in turn is connected to an output amplifier.

Buffer gates, transfer gates, readout registers, floating diffusion regions and output amplifiers are well known in CCDs and will not be described in more detail here. The configuration shown in FIG. 6 is merely by way of example to explain the operation of the line sensor. Different configurations of readout structures are possible without departing from the scope of the invention. In one exemplary embodiment a single transfer gate without any buffer gate could be used. In another exemplary embodiment multiple buffer gates could be used. In yet another exemplary embodiment, no readout register may be used and individual pixels, or pairs of pixels, may be connected through buffer and transfer gates to separate outputs. Details of commonly used semiconductor manufacturing processes that are not directly relevant to the invention are not included in order to avoid complicating the description.

Figure 7:
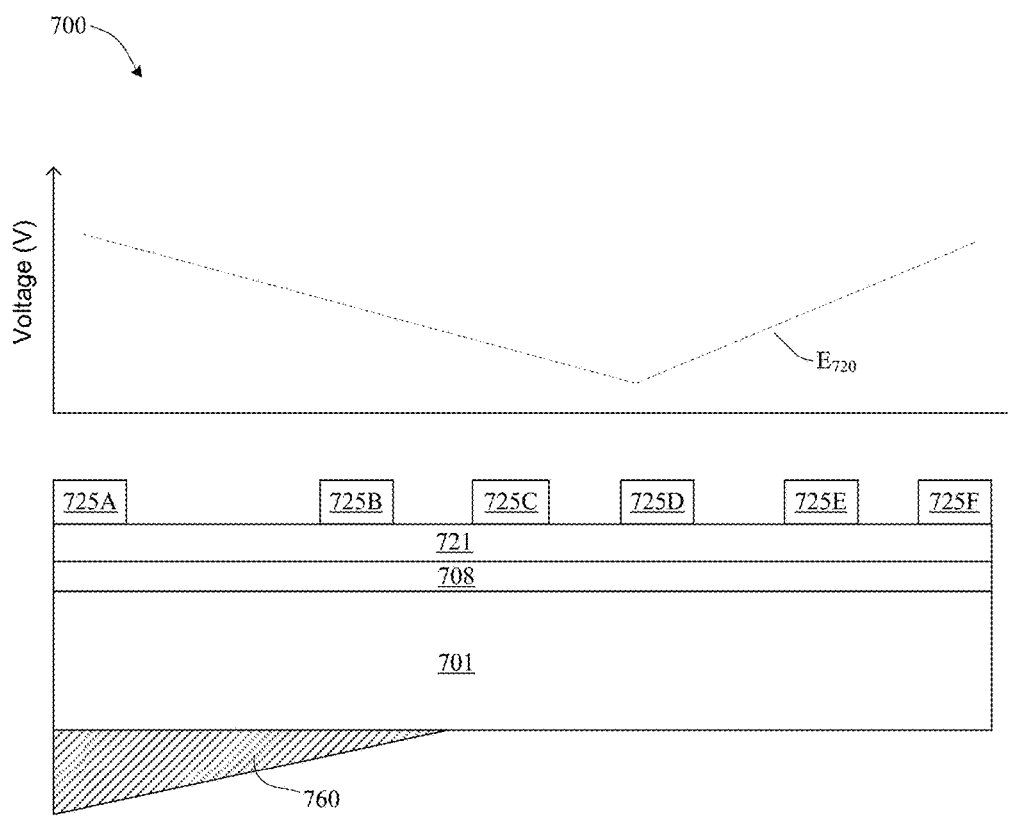
FIG. 7 is a cross-sectional view showing a simplified pixel of an exemplary line sensor according to another specific embodiment of the present invention.

FIG. 7 is a simplified cross-section showing a pixel of a linear sensor 700 including a wedge-shaped optical knife edge (mechanical aperture structure) 760 disposed on or over a backside surface of substrate 701 such that a portion of light reflected or otherwise directed to sensor 700 from a sample is blocked by optical knife edge 760. As in the previous embodiments, a resistive control gate 721 is formed on a dielectric layer 708 over a frontside surface of substrate 701, and multiple aperture control electrodes 725A to 725F are disposed on a upper surface of resistive control gate 721. In one embodiment, optical knife edge 760 is implemented using a slit aperture filter as taught in co-owned and co-pending U.S. patent application Ser. No. 14/691,966, filed Apr. 21, 2015 and entitled CONFOCAL LINE INSPECTION OPTICAL SYSTEM, which is incorporated herein by reference in its entirety. According to the present embodiment, a control circuit (not shown) of system 700 is configured to facilitate adjustment of aperture control voltages applied to electrodes 725A to 725F such that a non-monotonic voltage profile $E_{720}$ created in resistive control gate 721 adjusts the aperture to correct for misalignment of optical knife edge 760, thereby greatly simplifying the alignment process.

The various embodiments of the structures and methods of this invention that are described above are illustrative only of the principles of this invention and are not intended to limit the scope of the invention to the particular embodiments described. For example, more or fewer than four connections may be made to the resistive gate. In one embodiment of a method of inspecting or measuring a sample, one set of voltages may be applied to the contacts of a resistive gate on a sensor for the entire duration of the inspection or measurement on a sample. In another embodiment of a method of inspecting or measuring a sample, the voltages applied to the contacts of a resistive gate may be adjusted during the inspection or measurement of a single sample in order to adapt to different patterns in different locations on that sample.

It is also to be understood that where sensors or methods are described as detecting light that these descriptions may also apply to detecting electromagnetic radiation of different wavelengths including infra-red, visible light, ultra-violet, extreme UV and X-rays, and to detecting charged particles such as electrons.

Thus, the invention is limited only by the following claims and their equivalents.

The invention claimed is:

1. A method of inspecting a sample, the method comprising:
    directing and focusing radiation onto the sample;
    directing radiation received from the sample to a line sensor, wherein the line sensor includes at least one pixel disposed on a substrate, said pixel including a resistive control gate attached to an upper surface of the substrate and disposed over a light sensitive region of the substrate, and wherein directing the received radiation includes causing the directed light to enter the light sensitive region;
    driving the resistive control gate using predetermined aperture control signals such that the resistive control gate generates an electric field in said light sensitive region that drives first photoelectrons generated by first light portions in a first light sensitive portion of said pixel into a first charge accumulation region located adjacent to a first end portion of said resistive control gate, and drives second photoelectrons generated by second light portions in a second light sensitive portion of said pixel toward a second end portion of said resistive control gate.

2. The method of claim 1, further comprising measuring the first photoelectrons accumulated in the first charge accumulation region during a predetermined period.

3. The method of claim 2, wherein directing the radiation further comprises generating a confocal image including first confocal image portions directed from said sample into a first light sensitive portion of said light sensitive region of said pixel, and second confocal image portions directed from said sample into a second light sensitive portion of said light sensitive region of said pixel.

4. The method of claim 2, wherein directing the radiation further comprises directing first radiation portions disposed within a first range of angles from said sample into a first light sensitive portion of said light sensitive region of said pixel, and directing second radiation portions disposed within a second range of angles from said sample into a second light sensitive portion of said light sensitive region of said pixel.

5. The method of claim 1, wherein driving the resistive control gate of said pixel comprises generating first and second aperture control signals on first and second end electrodes that contact opposing end portions of said resistive control gate and generating a third aperture control signal on at least one central electrode that contacts a central portion of said resistive control gate.

6. The method of claim 5, wherein driving the resistive control gate further comprises:
    during a first time period, generating said first, second and third aperture control signals such that said first and second aperture control signals are more positive than said third aperture control signal, and
    during a second time period, generating said first, second and third aperture control signals such that said first aperture control signal is more positive than said second and third aperture control signals.

7. The method of claim 1, wherein driving the resistive control gate of said pixel comprises generating first and second aperture control signals on first and second end electrodes that respectively contact corresponding end portions of said resistive control gate, and generating third, fourth and fifth aperture control signals respectively on first, second and third central electrodes that respectively contact corresponding central portions of said resistive control gate, wherein said first, second and fourth aperture control signals are more positive than said third and fifth aperture control signals, whereby said resistive control gate of said pixel generates an electric field in said light sensitive region that drives said first photoelectrons into said first charge accumulation region, drives said second photoelectrons toward said second end portion of said resistive control gate, and drives third photoelectrons generated by third light portions in a third light sensitive portion of said pixel into a second charge accumulation region located between said first charge accumulation region and said second end portion of said resistive control gate.

8. The method of claim 7, wherein directing the radiation further comprises directing first radiation portions disposed within a first range of angles from said sample into said first light sensitive portion of said light sensitive region of said pixel, directing second radiation portions disposed within a second range of angles from said sample toward said second end portion, and directing third radiation portions disposed within a third range of angles from said sample into said second light sensitive portion of said light sensitive region of said pixel.

9. The method of claim 1,
wherein the line sensor includes a mechanical aperture structure disposed between a lower surface of the substrate and said sample, and
wherein driving the resistive control gate comprises adjusting said electric field to correct for misalignment of said mechanical aperture structure.

10. A sensor comprising:
a substrate having an upper surface and an opposing lower surface;
a plurality of pixels disposed on the substrate, each pixel including a resistive control gate attached to the upper surface and disposed over an associated light sensitive region of the substrate, and at least one transfer gate disposed adjacent to a first end portion of said resistive control gate;
a plurality of elongated aperture control electrodes extending in parallel across said resistive control gates of said plurality of pixels, said plurality of aperture control electrodes including a first end electrode contacting said first end portion of each said resistive control gate, a second end electrode contacting a second end portion of each said resistive control gate, and one or more central electrode contacting each said resistive control gate and disposed between said first and second end electrodes; and
a control circuit configured to simultaneously apply aperture control signals onto said resistive control gates of said plurality of pixels by way of said plurality of aperture control electrodes such that first and second aperture control signals applied to said first and second end electrodes are more positive than a third aperture control signal applied to said at least one central electrode, thereby causing each said resistive control gate to generate an electric field in said associated light sensitive region such that first photoelectrons generated by said first light portions in a first light sensitive portion of each said pixel are driven by said electric field into a first charge accumulation region located adjacent to said first end portion of each said resistive control gate, and such that second photoelectrons generated by second light portions in said second light sensitive portion of each said pixel are driven by said electric field toward said second end portion of each said resistive control gate.

11. The sensor of claim 10, further comprising a readout circuit including a plurality of readout registers, each said readout register being operably coupled to said at least one transfer gate of an associated pixel of said plurality of pixels,
wherein said control circuit is further configured to actuate the plurality of pixels and the readout circuit such that said first photoelectrons are transferred to said plurality of readout registers from said first charge accumulation regions by way of said at least one transfer gates of said plurality of pixels during a readout operation.

12. The sensor of claim 10,
wherein said one or more central electrode comprises at least three central electrodes, and
wherein the control circuit is configured to generate said aperture control signals such that third photoelectrons generated by third light portions in a third light sensitive portion of each said pixel are driven by said electric field into a second charge accumulation region located between said first charge accumulation region and said second end portion of each said resistive control gate.

13. The sensor of claim 10, wherein the substrate comprises epitaxial silicon layer, and wherein the sensor further comprises a pure boron layer formed over the lower surface of the epitaxial silicon layer.

14. The sensor of claim 10, wherein the substrate comprises epitaxial silicon layer, and wherein the sensor further comprises an anti-reflection layer formed over the lower surface of the epitaxial silicon layer.

15. A system for inspecting or measuring a sample, the system comprising:
an illumination source configured to generate light;
optics configured to direct said light from the illumination source to the sample, and to direct light from the sample to a sensor;
a sensor including:
a substrate having an upper surface and an opposing lower surface;
a plurality of pixels disposed on the substrate, each pixel including a resistive control gate attached to the upper surface and disposed over an associated light sensitive region of the substrate;
at least three aperture control electrodes extending across and electrically connected to said resistive control gate of each of said plurality of pixels, said at least three aperture control electrodes including first and second end electrodes respectively extending across opposing first and second end portions of each said resistive control gate, and one or more central electrode disposed between said first and second end electrodes;
a control circuit configured to simultaneously apply aperture control signals onto said resistive control gates of said plurality of pixels by way of said at least three aperture control electrodes such that each said resistive control gate generates an electric field in said associated light sensitive region that separates photoelectrons generated by light entering the associated light sensitive region into at least two portions; and at least one readout circuit disposed on at least one side of the plurality of pixels.

16. The system of claim 15, wherein said one or more central electrode comprises a plurality of central electrodes, and wherein the control circuit is configured to generate multiple combinations of said aperture control signals such that said electric field is adjustable by way of changing from one said combination to another said combination.

17. The system of claim 16, wherein said one or more central electrode comprises at least three central electrodes, and wherein the control circuit is configured to generate said aperture control signals such that said photoelectrons are divided into at least three portions.

18. The system of claim 17, wherein said optics are further configured such that first light portions directed within a first range of angles from said sample to said sensor are directed into a first light sensitive portion of said associated light sensitive region of each said pixel, and such that second light portions directed within a second range of angles from said sample to said sensor are directed into a second light sensitive portion of said associated light sensitive region of each said pixel, and wherein said resistive control gate generates said electric field such that first photoelectrons generated by said first light portions in said first light sensitive portion of each said pixel are driven by said electric field into a first charge accumulation region located adjacent to said first end portion of each said resistive control gate, and such that second photoelectrons generated by said second light portions in said second light sensitive portion of each said pixel are biased by said electric field toward said second end portion of each said resistive control gate.

19. The system of claim 15, wherein the substrate comprises a semiconductor membrane, and wherein the sensor further comprises a pure boron layer deposited on the lower surface of the semiconductor membrane.

20. The system of claim 15, further comprising a mechanical aperture structure disposed adjacent to a lower surface of the substrate such that a portion of the light from said sample is blocked by said mechanical aperture structure, wherein said control circuit is further configured to adjust said electric field in accordance with a misalignment of said mechanical aperture structure relative to said sensor.

* * * * *